(12) United States Patent
Coppens et al.

(10) Patent No.: US 12,320,875 B2
(45) Date of Patent: Jun. 3, 2025

(54) COIL POSITIONING APPARATUSES, SYSTEMS, AND METHODS THEREOF

(71) Applicant: Qfix Systems, LLC, Avondale, PA (US)

(72) Inventors: Daniel D. Coppens, Avondale, PA (US); Josef Gabelberger, Avondale, PA (US); Andrew Johnson, Avondale, PA (US); David M. Rabeno, Avondale, PA (US)

(73) Assignee: Qfix Systems, LLC, Avondale, PA (US)

( * ) Notice: Subject to any disclaimer, the term of this patent is extended or adjusted under 35 U.S.C. 154(b) by 476 days.

(21) Appl. No.: 17/286,663

(22) PCT Filed: May 16, 2019

(86) PCT No.: PCT/US2019/032630
§ 371 (c)(1),
(2) Date: Apr. 19, 2021

(87) PCT Pub. No.: WO2020/081123
PCT Pub. Date: Apr. 23, 2020

(65) Prior Publication Data
US 2021/0369133 A1  Dec. 2, 2021

Related U.S. Application Data

(60) Provisional application No. 62/748,013, filed on Oct. 19, 2018.

(51) Int. Cl.
| | | |
|---|---|---|
| *G01R 33/34* | (2006.01) | |
| *A61B 5/00* | (2006.01) | |
| *A61B 5/055* | (2006.01) | |

(52) U.S. Cl.
CPC ........ *G01R 33/34084* (2013.01); *A61B 5/055* (2013.01); *A61B 5/704* (2013.01)

(58) Field of Classification Search
CPC ..... A61B 5/0033; A61B 5/055; A61B 5/6814; A61B 5/704; G01R 33/34084
See application file for complete search history.

(56) References Cited

U.S. PATENT DOCUMENTS

| | | |
|---|---|---|
| 9,775,934 B2 | 10/2017 | Coppens |
| 2008/0251672 A1* | 10/2008 | Barton .................. A61B 90/50 |
| | | 248/323 |

(Continued)

FOREIGN PATENT DOCUMENTS

| | | |
|---|---|---|
| WO | 2018097861 A1 | 5/2018 |
| WO | WO 2018/097860 | * 5/2018 |

OTHER PUBLICATIONS

Corea et al., "Materials and methods for higher performance screen-printed flexible MRI receive coils", Magn. Reson. Med., Aug. 2017 ; 78(2): 775-783.

(Continued)

*Primary Examiner* — Christopher L Cook
(74) *Attorney, Agent, or Firm* — Buchanan Ingersoll & Rooney PC

(57) ABSTRACT

Aspects of the invention are directed to coil positioning apparatuses, systems, and methods of employing the same. One portable head coil apparatus is provided for use with a magnetic resonance imaging system. The portable head coil apparatus includes a base having at least one coil array comprising at least two coil elements. The base is positionable relative to the patients head and has a receiving portion defining a receiving surface positionable adjacent the patient positioning device. The portable head coil apparatus includes an extension movable relative to the base and having at least one coil array comprising at least two coil elements. The extension defines an inner surface having a curvature the degree of which is greater than that of the receiving surface of the base. The inner surface of the (Continued)

extension and the receiving surface of the base together at least partially define an imaging region therebetween.

30 Claims, 40 Drawing Sheets

(56) References Cited

U.S. PATENT DOCUMENTS

| | | | |
|---|---|---|---|
| 2009/0306495 A1 | 12/2009 | Scarth et al. | |
| 2011/0040174 A1* | 2/2011 | Driemel | G01R 33/36 |
| | | | 600/422 |
| 2012/0265052 A1 | 10/2012 | Rohr et al. | |
| 2012/0268116 A1 | 10/2012 | Zhu et al. | |
| 2013/0317346 A1* | 11/2013 | Alagappan | G01R 33/34046 |
| | | | 600/415 |
| 2014/0191753 A1* | 7/2014 | Oh | G01R 33/4835 |
| | | | 324/309 |
| 2016/0206395 A1 | 7/2016 | Coppens et al. | |

OTHER PUBLICATIONS

International Preliminary Report for International Application No. PCT/US2019/032630, dated Apr. 14, 2021, 16 pages.
International Search Report and Written Opinion for International Application No. PCT/US2019/032630, dated Oct. 17, 2019, 19 pages.

* cited by examiner

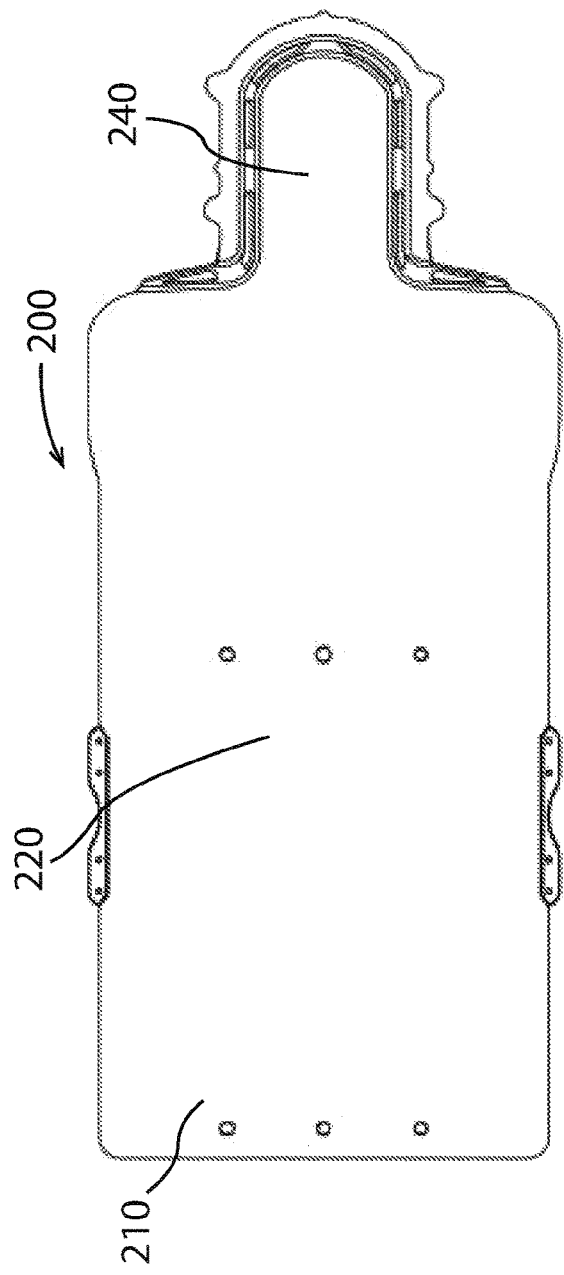
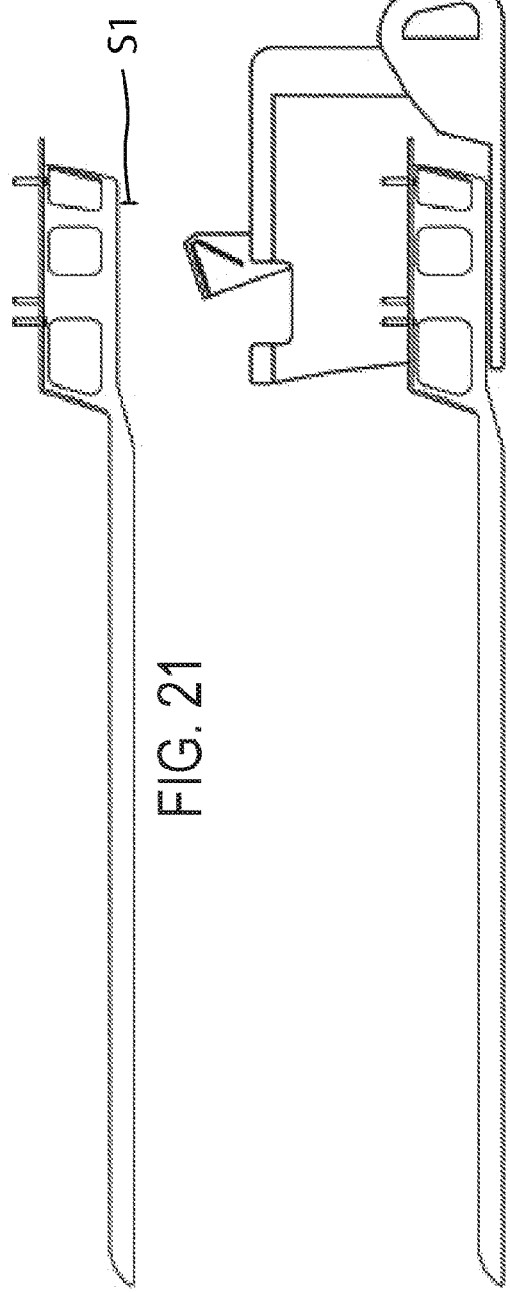
FIG. 20  FIG. 21  FIG. 22

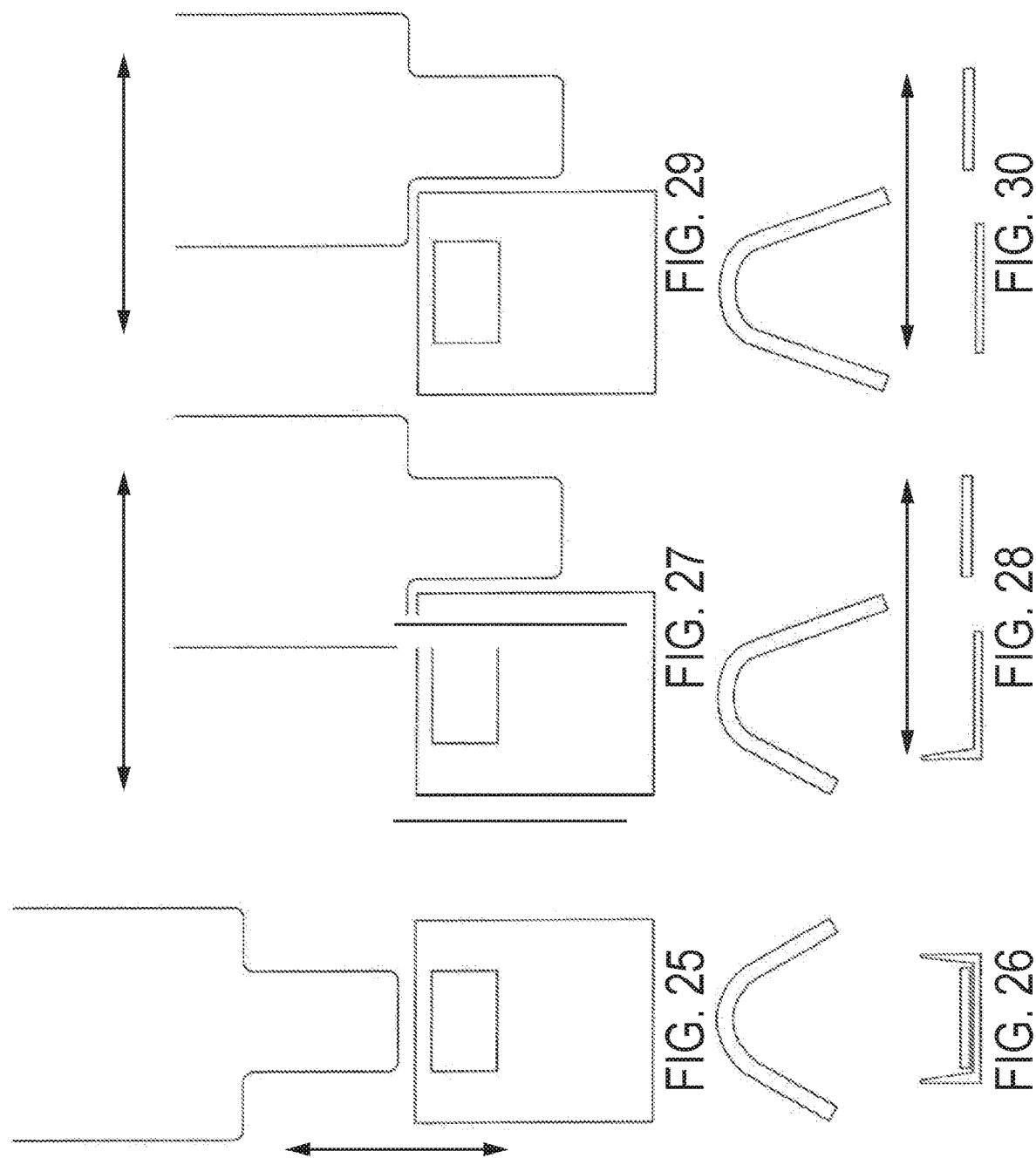

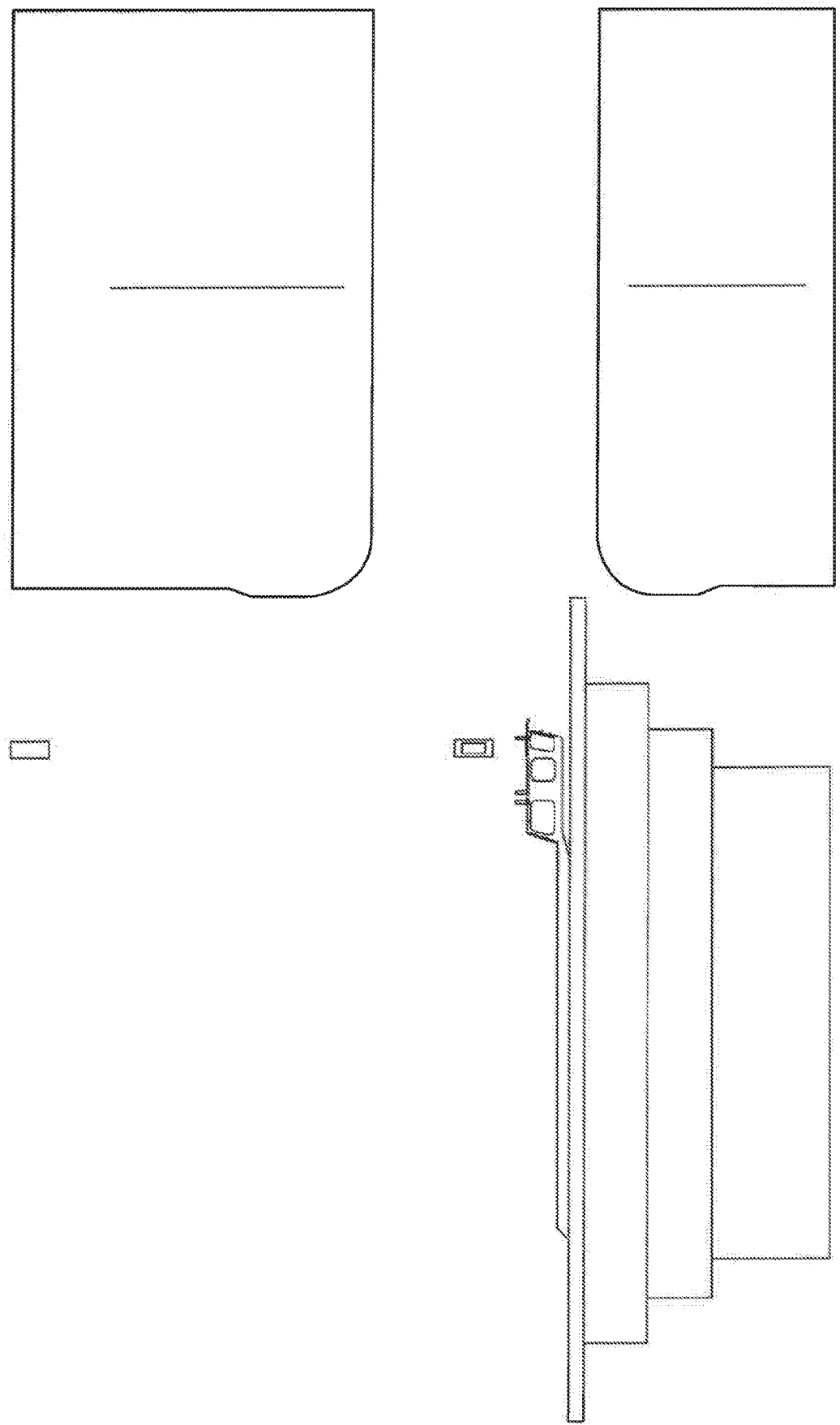

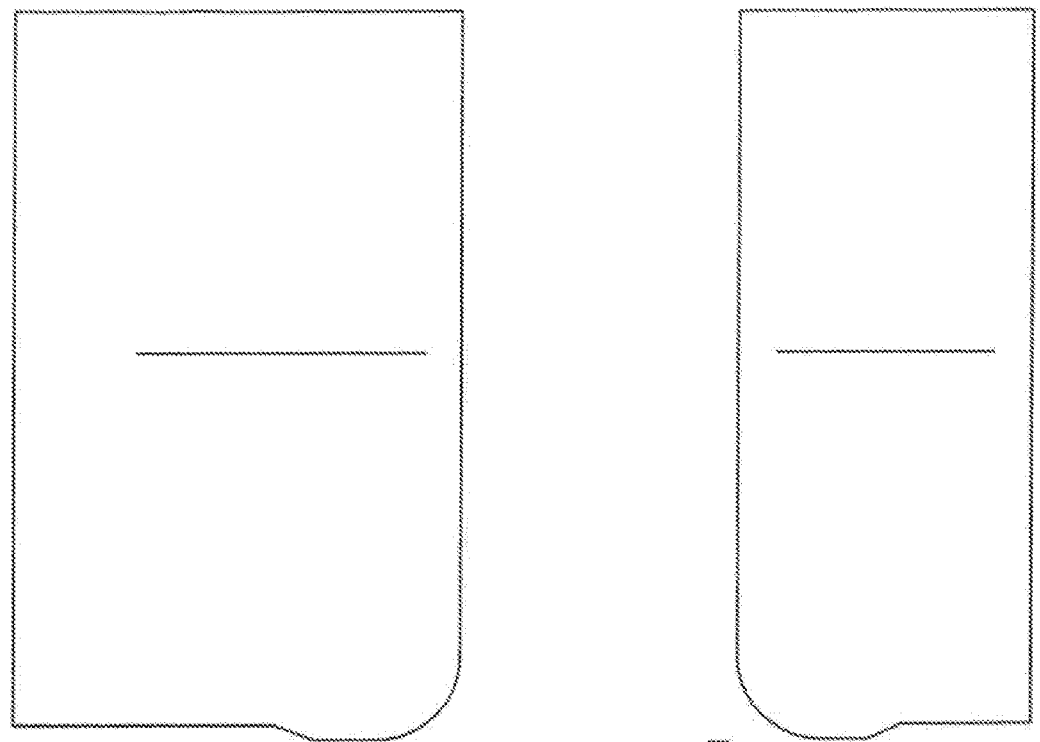
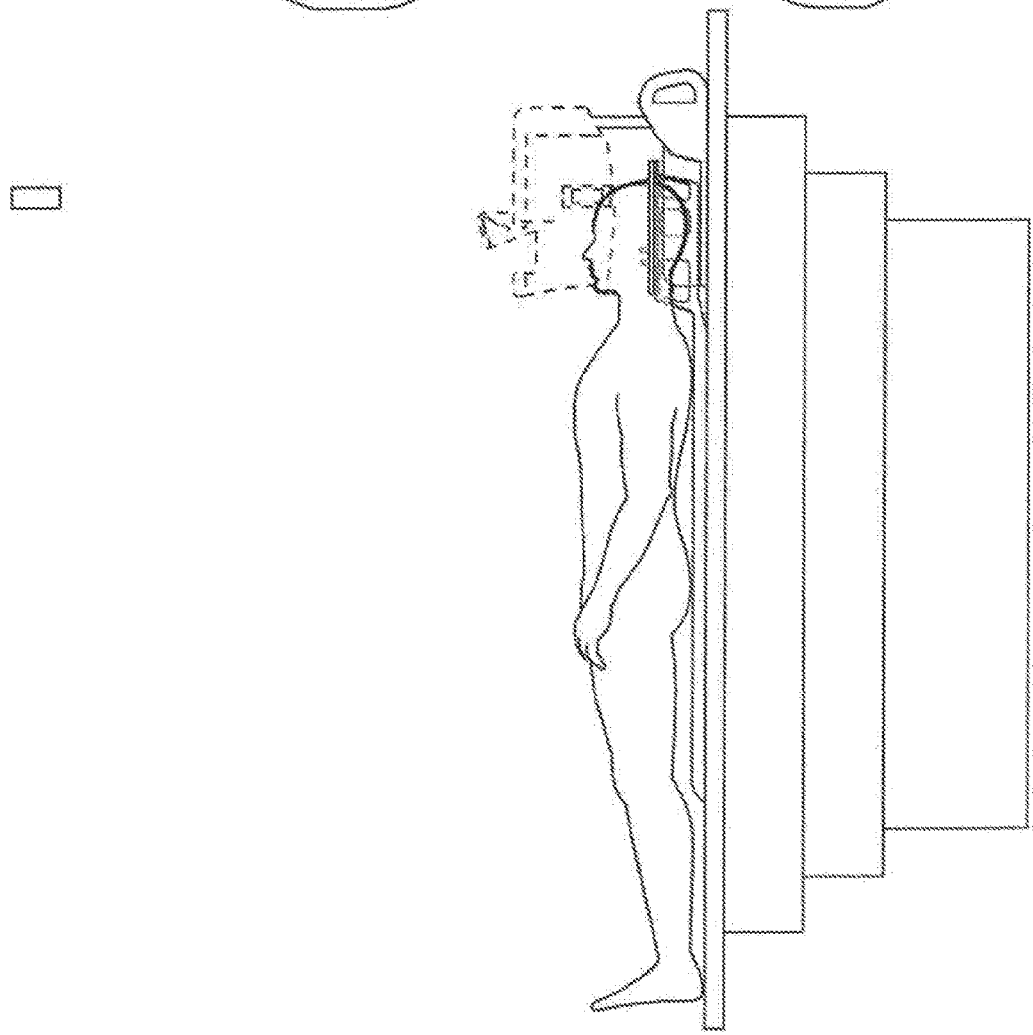
FIG. 39

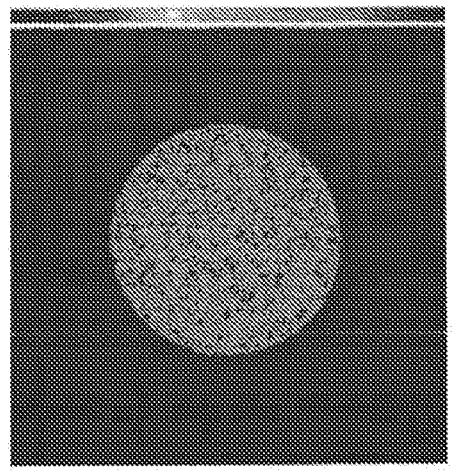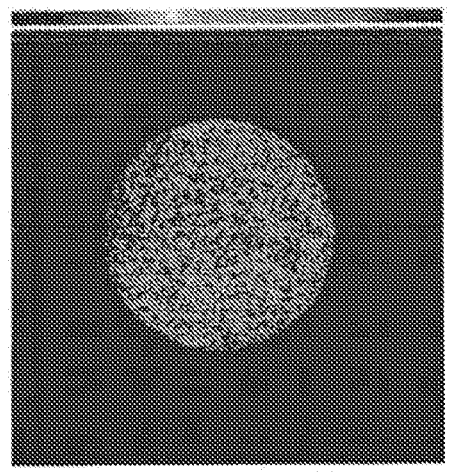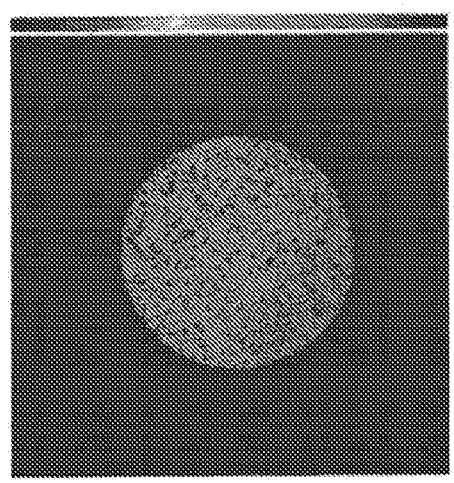
FIG. 47A

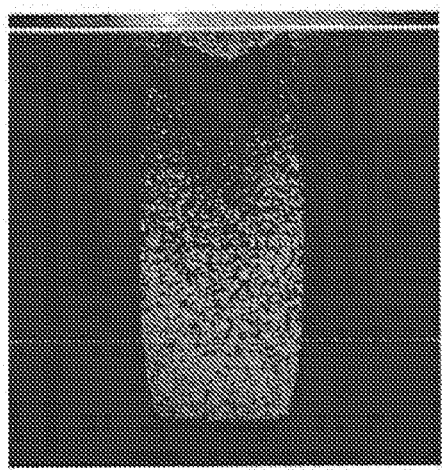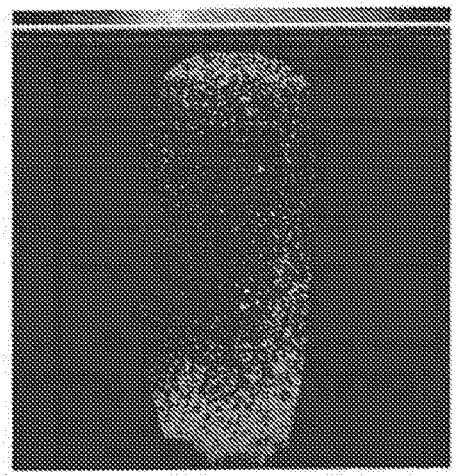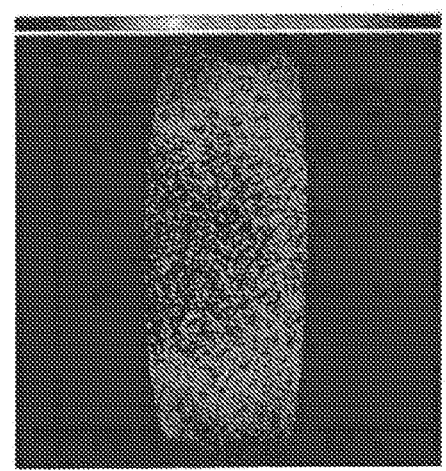
FIG. 47B

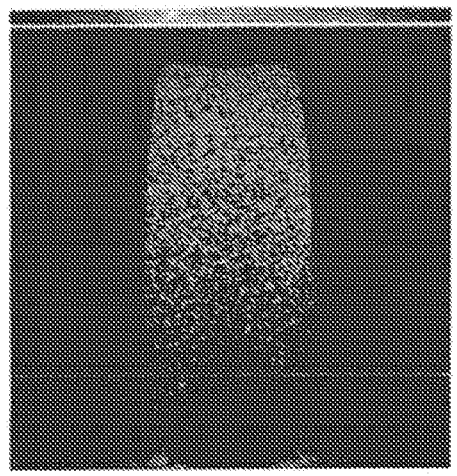
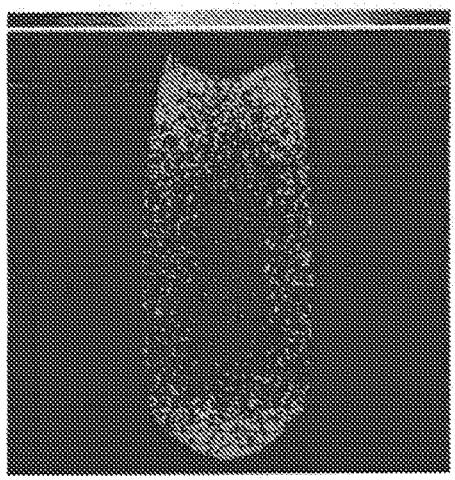
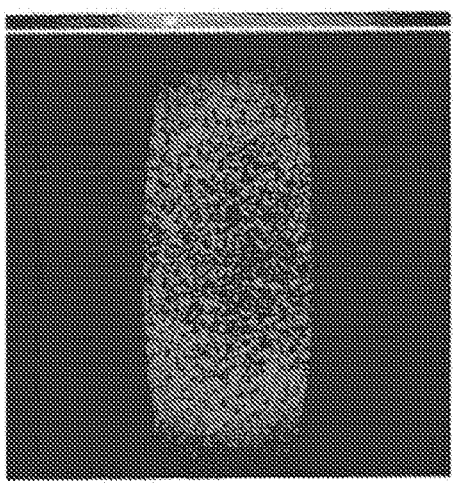
FIG. 47C

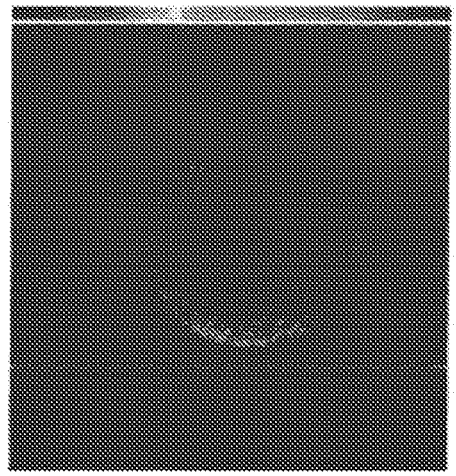
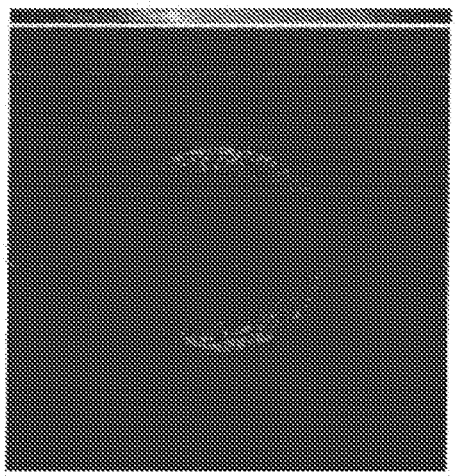
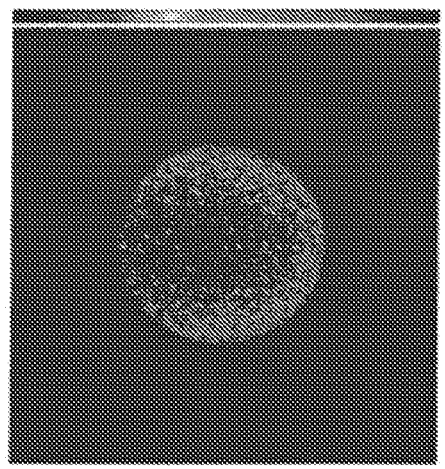
FIG. 47F

COIL POSITIONING APPARATUSES, SYSTEMS, AND METHODS THEREOF

CROSS-REFERENCE TO RELATED APPLICATIONS

This application is the National Stage of PCT International Application No. PCT/US2019/032630, filed May 16, 2019, which claims the benefit of U.S. Provisional Application No. 62/748,013, filed Oct. 19, 2018, the contents of which are incorporated herein by reference in their entireties for all purposes.

FIELD OF THE INVENTION

The present invention is directed to coil positioning apparatuses, systems, and methods of employing the same.

BACKGROUND OF THE INVENTION

Diagnosing and treating a patient often requires precise imaging and treatment procedures. To improve the accuracy and precision of diagnosis and treatment procedures, a patient may be submitted to imaging from several imaging modalities and/or submitted to one or more imaging modalities prior to treatment procedures. Thus, a patient may be transported to several modalities during a diagnosis or treatment procedure. Transporting a patient to various modalities of diagnosis or treatment is generally time consuming and labor intensive.

In certain situations, a patient undergoing a critical medical condition may be required to forego imaging from certain modalities due to the time-consuming nature of transporting and repositioning the patient and the time sensitivity of the critical medical condition. For example, in stroke or heart attack victims, the length of time between the adverse medical condition and treatment may reduce the ability of the patient to recover. Thus, stroke or heart attack victims may require quick and decisive treatment without submitting the patient to an ideal imaging procedure using a plurality of imaging modalities.

Additionally, in recent years, healthcare costs have become of greater public concern. The capital, labor, and time costs associated with diagnosis and treatment procedures that utilize more than one imaging and/or treatment modalities contributes to increasing the overall cost of healthcare.

Accordingly, there is a need for more time and cost-efficient systems, methods, and apparatus for diagnosing and/or treating a patient using one or more modalities.

SUMMARY OF THE INVENTION

Aspects of the invention are directed to coil positioning apparatuses, systems, and methods of employing the same.

In accordance with one aspect of the invention, a portable head coil apparatus is provided for use with a magnetic resonance imaging system. The portable head coil apparatus is configured for unrestricted movement relative to a patient's head supported by a patient positioning device. The portable head coil apparatus includes a base having at least one coil array comprising at least two coil elements. The base being positionable relative to the patient's head to facilitate imaging of the patient's head by the at least one coil array, and the base having a receiving portion defining a receiving surface positionable adjacent the patient positioning device. The portable head coil apparatus further comprises an extension movable relative to the base and having at least one coil array comprising at least two coil elements. The extension defines an inner surface having a curvature the degree of which is greater than that of the receiving surface of the base. The inner surface of the extension and the receiving surface of the base together at least partially define an imaging region therebetween for receiving the patient's head supported on the patient positioning device. The imaging region extends from a superior end of the portable head coil apparatus to an inferior end of the portable head coil apparatus and is accessible from both the superior end and the inferior end of the portable head coil apparatus. In addition, the portable head coil apparatus includes an arm coupled to the base and the extension. The arm is configured to space the base from the extension and to adjust the position of the extension relative to the base between an extended position in which the extension is spaced from the base and an imaging position in which the extension is adjacent to the base. At least one of the coil elements of the at least one coil array of the extension is not parallel to an adjacent one of the coil elements of the at least one coil array of the base in the imaging position.

According to a further aspect, provided is a system including a portable head coil apparatus and a patient positioning device. The patient positioning device includes a head portion adapted to support a patient's head. The head portion has a head support surface and an opposed surface. The patient positioning device includes a body portion coupled to the head portion and adapted to support the body of the patient. The body portion has a body support surface and an opposed surface extending generally in an opposed surface plane. The opposed surface of the head portion is spaced from the opposed surface plane of the body portion, such that the opposed surface of the head portion at least partially defines a space between the opposed surface of the head portion and the opposed surface plane of the body portion. The portable head coil apparatus includes a base having at least one coil array comprising at least two coil elements. The base being positionable relative to the patient's head to facilitate imaging of the patient's head by the at least one coil array, and the base having a receiving portion defining a receiving surface positionable adjacent the patient positioning device. The portable head coil apparatus further comprises an extension movable relative to the base and having at least one coil array comprising at least two coil elements. The extension defines an inner surface having a curvature the degree of which is greater than that of the receiving surface of the base. The inner surface of the extension and the receiving surface of the base together at least partially define an imaging region therebetween for receiving the patient's head supported on the patient positioning device. In addition, the portable head coil apparatus includes an arm coupled to the base and the extension. The arm is configured to space the base from the extension and to adjust the position of the extension relative to the base between an extended position in which the extension is spaced from the base and an imaging position in which the extension is adjacent to the base. At least one of the coil elements of the at least one coil array of the extension is not parallel to an adjacent one of the coil elements of the at least one coil array of the base in the imaging position.

In accordance with another aspect of the invention, a coil apparatus is provided for use in a magnetic resonance imaging system. The coil apparatus is configured to be movable relative to a patient. The coil apparatus includes a base comprising at least one coil array, the base being positionable to facilitate imaging by the at least one coil array; an extension comprising at least one coil array, the extension being spaced from the base by a distance; and at least one arm coupled to the base and the extension. The at least one arm spacing the base from the extension.

According to still another aspect of the invention, a patient positioning apparatus is provided for positioning a patient within an imaging system. The patient positioning apparatus includes a support structure having a head portion adapted to receive a head of a patient and a body portion adapted to receive the body of a patient, the head portion comprising a recess underneath it adapted to receive a MRI coil.

In accordance with yet another aspect of the invention, a coil positioning system is provided. The coil positioning system comprises a head coil apparatus configured to be moveable to a patient and to receive a portion of a patient positioning apparatus. The head coil apparatus including: a base comprising at least one coil array, the base being positionable to facilitate imaging by the at least one coil array; an extension comprising at least one coil array, the extension being spaced from the base by a distance; and an arm coupled to the base and the extension, the at least one coil array of the base and the at least one coil array of the extension defining an interior region therebetween.

According to another aspect of the invention, provided is an imaging system including a head coil apparatus configured to be moveable to a patient and to receive a portion of a patient positioning apparatus, a patient positioning apparatus having a support structure, and an imaging scanner.

In accordance with yet another aspect, a method is provided for positioning a head coil apparatus relative to a patient for imaging. The method comprises positioning a base including a first coil array to facilitate imaging of the patient by the first coil array by moving the base in a positioning direction; positioning an extension including a second coil array to facilitate imaging of the patient by the second coil array by moving the extension relative to the base along an extending direction, thereby at least partially defining an interior region for receiving a body part of a patient to be imaged, the extending direction being orthogonal to the positioning direction; and retaining a selected distance between the first coil array and the second coil array along the extending direction, thereby maintaining the size of the interior region at least partially defined by the extension and the base.

According to an additional aspect, a head coil apparatus is provided for use with a magnetic resonance imaging system. The head coil apparatus is configured to be moveable relative to a patient and includes a base having at least one coil array. The base is positionable to facilitate imaging by the at least one coil array and has a receiving portion defining a receiving surface. The head coil apparatus further includes an extension movable relative to the base. The extension has at least one coil array and defines an inner surface having a curvature the degree of which is greater than that of the receiving surface of the base. The inner surface of the extension and the receiving surface of the base together at least partially defining a receiving space therebetween for receiving the head of a patient positioned on a patient positioning device. Furthermore, the head coil apparatus includes at least one arm coupled to the base and the extension and configured to space the base from the extension and adjust the position of the extension relative to the base into an imaging position, wherein the at least one coil array of the extension is positionable proximal to the at least one coil array of the base in the imaging position.

In accordance with yet an additional aspect, a system is provided having a patient positioning device and a head coil apparatus and configured for use with an imaging device. The system includes a patient positioning device having: a head portion adapted to support a head of a patient, the head portion having a head support surface and an opposed surface; a body portion coupled to the head portion and adapted to support the body of the patient, the body portion having a body support surface and an opposed surface extending generally in an opposed surface plane. The opposed surface of the head portion is spaced from the opposed surface plane of the body portion, such that the opposed surface of the head portion at least partially defines a space between the opposed surface of the head portion and the opposed surface plane of the body portion. The system also includes a head coil apparatus configured to be moveable relative to a patient positioned on the patient positioning device and to receive at least the head portion of the patient support. The head coil includes: a base having a receiving surface and at least one coil array corresponding to the receiving surface, the base being positionable to facilitate imaging by the at least one coil array element; and an interior receiving portion at least partially defined by the receiving surface of the base. The interior receiving portion of the head coil is configured to receive at least the head of the patient and at least the head portion of the patient positioning device with the receiving surface of the base facing the opposed surface of the head portion of the patient positioning device. At least a portion of the base and at least a portion of the at least one coil array correspond to the receiving surface of the base and are configured to be received in the space defined between the opposed surface of the head portion of the patient support and the opposed surface plane of the body portion of the patient support.

Yet, according to another aspect, a system having a patient positioning device and a head coil apparatus is provided for use with an imaging device. The system includes a patient positioning device having: a head portion adapted to support a head of a patient; and a body portion coupled to the head portion and adapted to support the body of the patient; a patient support on which the patient positioning device is positionable, the patient support having at least one coil array element; and a head coil configured to be moveable relative to a patient positioned on the patient positioning device and to receive at least the head portion of the patient positioning device. The head coil at least partially defines an interior receiving portion configured to receive at least the head of the patient and at least the head portion of the patient positioning device.

In accordance with a further aspect, provided is a patient imaging system including an imaging scanner defining an imaging space; a laser alignment system associated with the imaging scanner; an MRI table movable relative to the imaging space of the imaging scanner; a patient positioning device supportable by the MRI table and having a head portion configured to support the head of a patient; and a head coil configured to be moveable relative to a patient positioned on the patient positioning device and to receive at least the head portion of the patient positioning device. The head coil includes a base having a receiving surface and at least one coil array element corresponding to the receiving surface; an interior receiving portion at least partially defined by the receiving surface of the base; and an indicia configured to be used in aligning the head coil using the laser alignment system. The base is positionable to facilitate imaging by the at least one coil array element.

According to another aspect of the invention, a method is provided for positioning a head coil relative to a patient. The method includes positioning a patient positioning device on a surface of a patient support such that an opposed surface of a head portion of the patient positioning device at least partially defines a space between the opposed surface of the head portion of the patient positioning device and the surface of the patient support; positioning a patient on the patient positioning device; and moving a head coil to the patient positioned on the patient positioning device such that an interior receiving portion of the head coil receives the head of the patient and the head portion of the patient positioning device with at least a portion of a base of the head coil and at least a portion of at least one coil array of the head coil received in the space defined between the opposed surface of the head portion of the patient positioning device and the surface of the patient support.

According to a further aspect, a head coil apparatus is provided for use with a magnetic resonance imaging system. The head coil apparatus includes an extension having at least one coil array and defining an inner surface having a curvature, such that the extension is configured to surround at least a portion of a patient's head. The extension of the head coil apparatus is configured to be coupled to and positioned with respect to a patient positioning device or a patient support having at least one coil array for imaging the patient's head. The curvature of the extension is greater than that of a surface of the patient positioning device or the patient support that is opposed to the inner surface of the extension.

In accordance with yet a further aspect, a head coil system is provided for use with a magnetic resonance imaging system. The head coil system includes an extension having a first coil array element; a patient positioning device or a patient support having a second coil array element; and at least one arm configured to couple the extension to the patient positioning device or the patient support. The extension also defines an inner surface having a curvature. The patient positioning device or the patient support is positionable relative to the extension and defines a surface. The surface of the patient positioning device or the patient support and the inner surface of the extension together at least partially define a receiving space therebetween for receiving the head of a patient. The at least one arm is configured to space the extension from the patient positioning device or the patient support and to adjust the position of the extension relative to the patient positioning device or the patient support into an imaging position.

According to another aspect of the invention, a head coil system has a patient positioning device and a head coil apparatus and is configured for use with an imaging device. The patient positioning device includes a head portion adapted to support a head of a patient, the head portion having a head support surface and an opposed surface; and a body portion coupled to the head portion and adapted to support the body of the patient, the body portion having a body support surface and an opposed surface extending generally in an opposed surface plane. The opposed surface of the head portion is spaced from the opposed surface plane of the body portion, such that the opposed surface of the head portion at least partially defines a space between the opposed surface of the head portion and the opposed surface plane of the body portion. The head coil apparatus is configured to be positionable relative to a patient positioned on the patient positioning device, the head coil apparatus including a base having a receiving surface and at least one base coil array corresponding to the receiving surface, the base being positionable to facilitate imaging by the at least one base coil array element. The base and the at least one base coil array are sized to extend into the space defined between the opposed surface of the head portion of the patient positioning device and the opposed surface plane of the body portion of the patient positioning device, the at least one base coil array being flexible for adjustment from a substantially flat configuration to an imaging configuration that partially surrounds the head of the patient. The head coil apparatus also includes an extension having a receiving surface and at least one extension coil array corresponding to the receiving surface, the extension being positionable to facilitate imaging by the at least one extension coil array element. The at least one extension coil array is flexible for adjustment from a substantially flat configuration to an imaging configuration that partially surrounds the head of the patient. The at least one base coil array and the at least one extension coil array are configured to be positioned such that the at least one base coil array and the at least one extension coil array together surround the head of the patient.

According to another aspect, the invention provides a method of positioning a head coil relative to a patient for imaging. The method includes positioning a patient positioning device on a surface of a patient support such that an opposed surface of a head portion of the patient positioning device at least partially defines a space between the opposed surface of the head portion of the patient positioning device and the surface of the patient support. It also includes positioning a patient on the patient positioning device, extending a base of a head coil into the space defined between the opposed surface of the head portion of the patient positioning device and the surface of the patient support, flexing at least one base coil array of the base from a substantially flat configuration to an imaging configuration that partially surrounds the head of the patient, and flexing at least one extension coil array of an extension of the head coil such that the at least one base coil array and the at least one extension coil array together surround the head of the patient.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. It is emphasized that according to common practice, the various features of the drawings may not be drawn to scale unless otherwise indicated. On the contrary, the dimensions of the various features may be expanded or reduced for clarity. Included in the drawings are the following figures:

FIGS. 20 and 21 are top and side views of a first embodiment of a patient positioning apparatus in accordance with aspects of the invention;

FIG. 22 is a side view of the patient positioning apparatus of FIGS. 20 and 21 with a head portion received within an internal region of a head coil apparatus;

FIGS. 25 and 26 are schematics depicting a first method of positioning a coil apparatus relative to a patient positioning apparatus;

FIGS. 27 and 28 are schematics depicting a second method of positioning a coil apparatus relative to a patient positioning apparatus;

FIGS. 29 and 30 are schematics depicting a third method of positioning a coil apparatus relative to a patient positioning apparatus;

FIGS. 34-43 is a schematic of a method of positioning a patient relative to a patient positioning apparatus, coil apparatus, and imaging system in accordance with aspects of the invention;

FIGS. 47A-47F are comparisons of the performance of the portable coil apparatus based on signal to noise ratio (SNR) and homogeneity against two exemplar coils devices.

DETAILED DESCRIPTION OF EMBODIMENTS OF THE INVENTION

Figure 1:
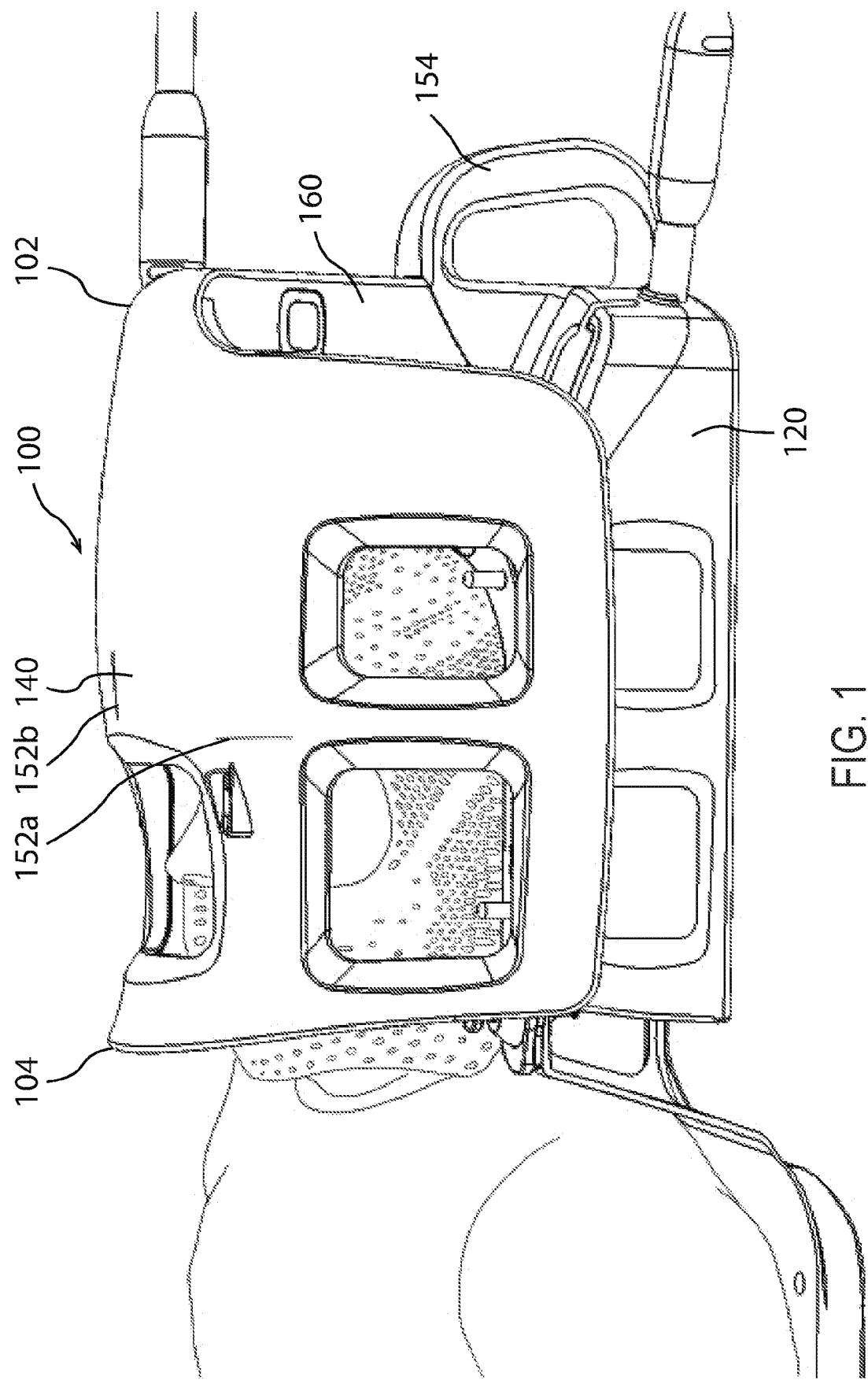
FIGS. 1-10 are perspective, front, top, side, rear perspective, and rear views of a first embodiment of a coil apparatus in accordance with aspects of the present invention.
Figure 2:
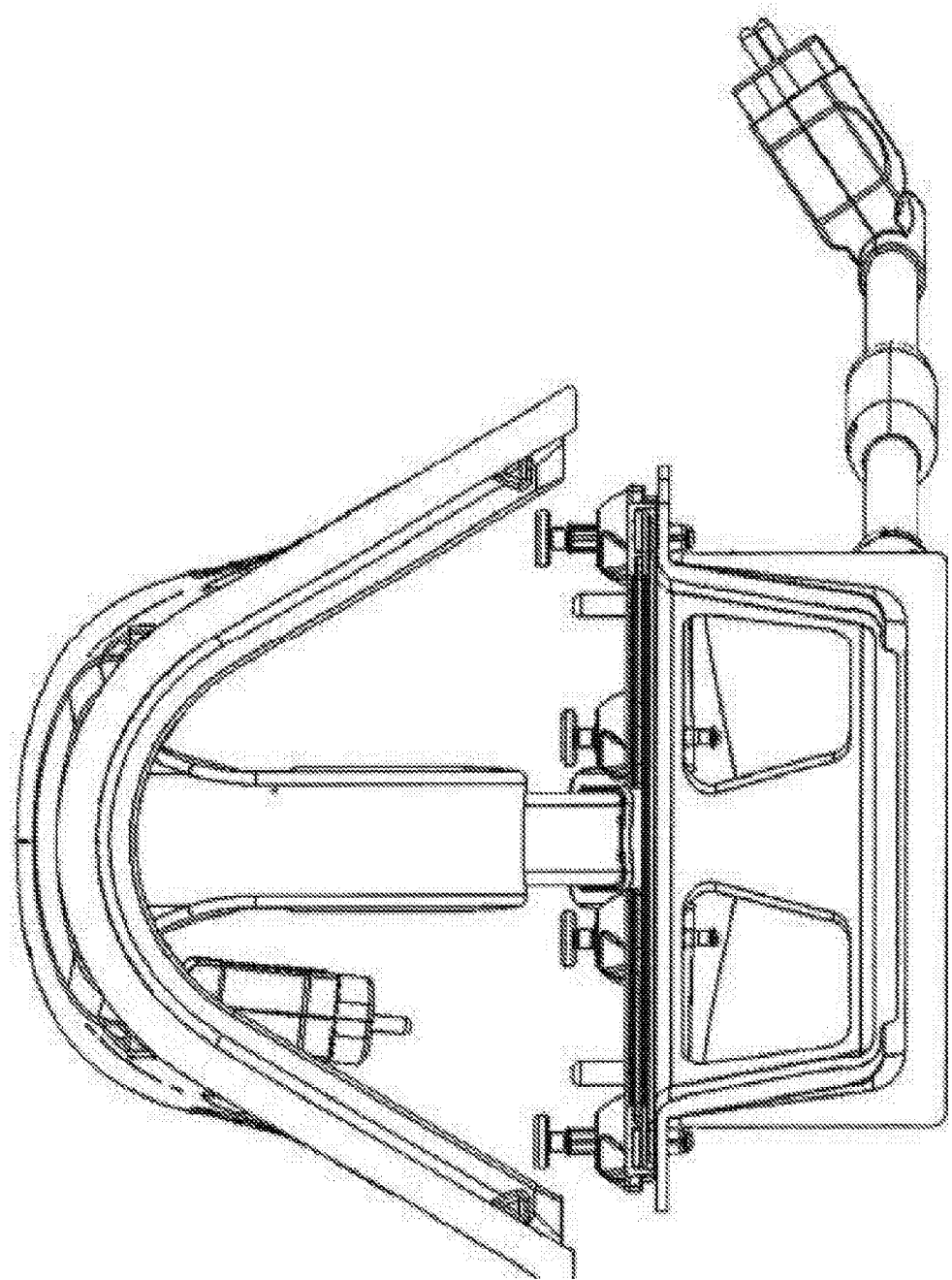
Figure 3:
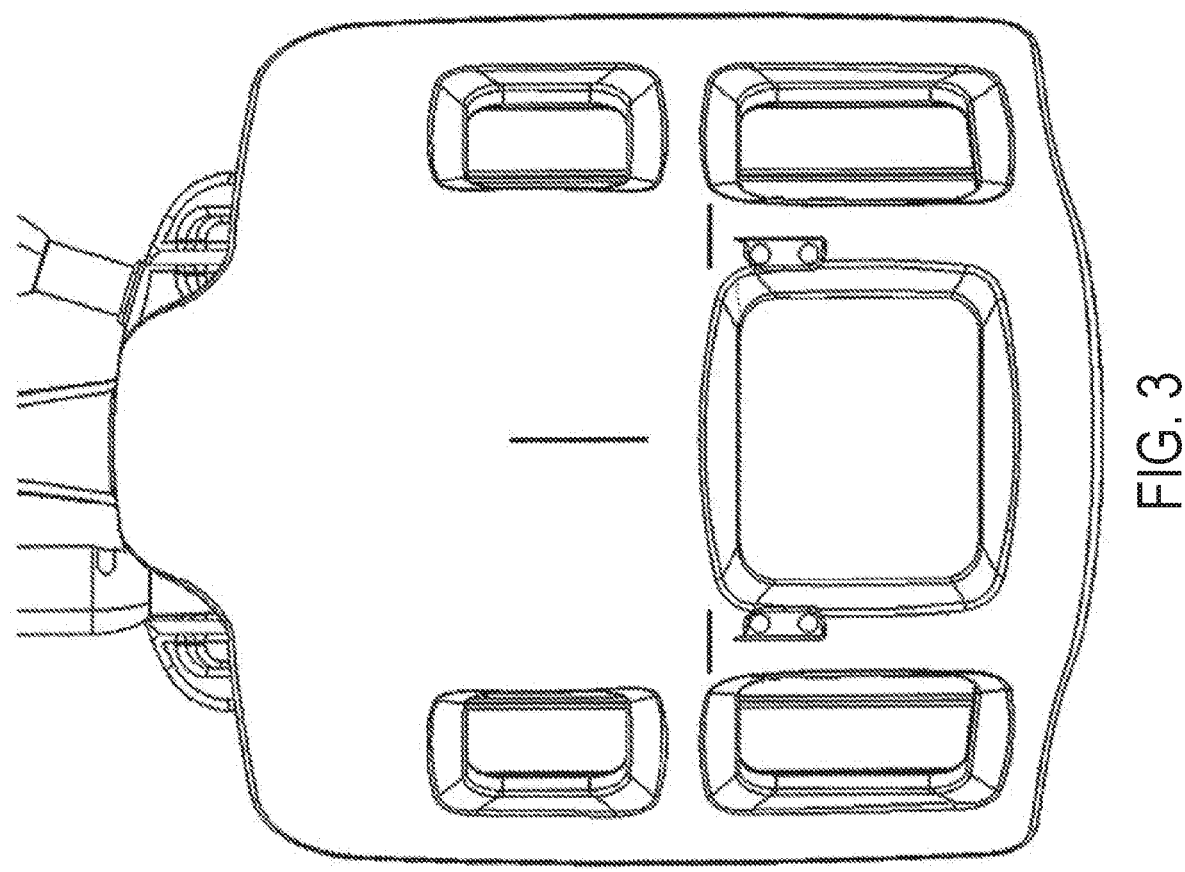
Figure 4:
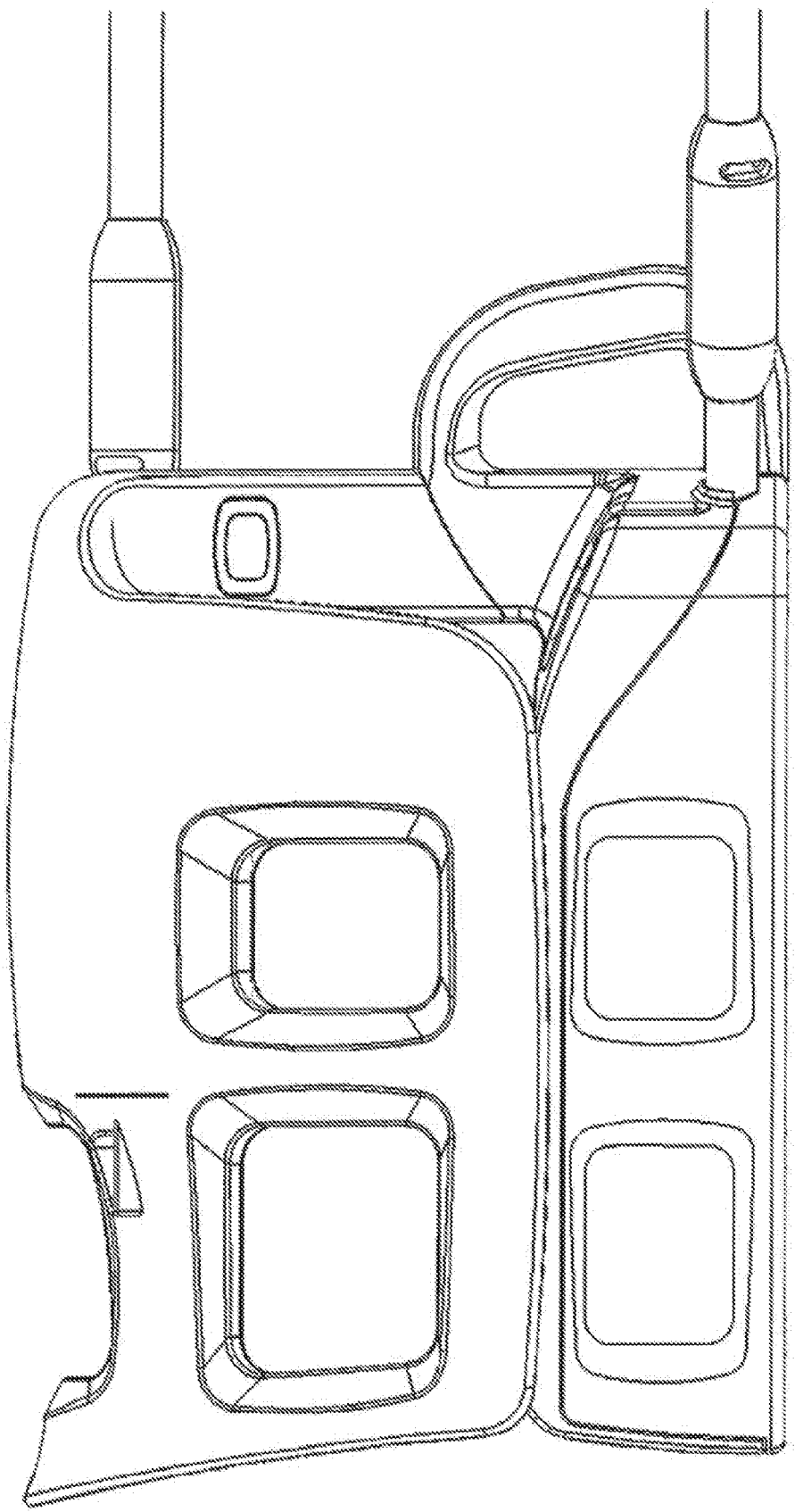
Figure 5:
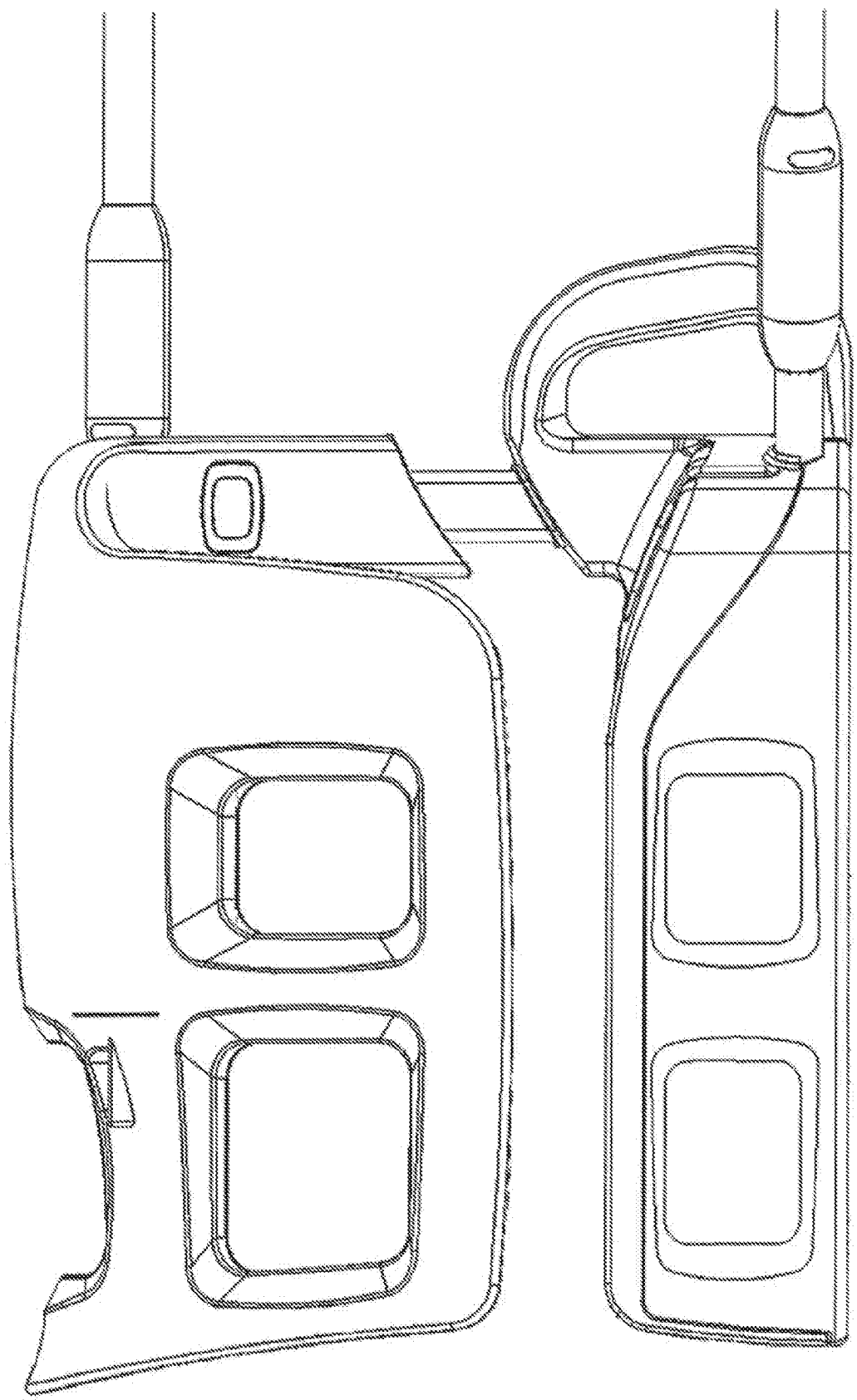

According to one aspect of the invention, a portable head coil apparatus 100 is provided for use in a magnetic resonance imaging system. The portable head coil apparatus 100 may be configured to be moveable relative to a patient. The portable head coil apparatus 100 may include: a base 120 comprising at least one coil array 122 (e.g., formed of at least one coil element/loop), the base 120 being positionable to facilitate imaging by the at least one at coil element 122; an extension 140 comprising at least one coil array 142 (e.g., formed of at least one coil element/loop), the extension 140 being spaced from the base by a distance d1; and at least one arm 160 coupled to the base 120 and the extension 140, which spaces the base 120 from the extension 140.

The extension 140 of the portable head coil apparatus 100 may be sized or configured to image various portions of a patient's anatomy. For example, the extension may be limited in size or shape to image a patient's head or may extend farther, such as extending to the patient's neck, past the patient's shoulders for imaging of the head to the pelvic region, or farther to extend the entire length of the patient. In one embodiment, for example, the extension may feature a head portion as well as a flexible removable component for widening the imaging field down to the pelvic region or beyond.

The base 120 of the portable head coil apparatus 100 may also be sized or configured to image various portions of a patient's anatomy. For example, the base may also extend past the patient's shoulders, potentially to the pelvis or beyond to the entire length of the patient to enable imaging studies of the spine and abdomen and other anatomies.

The portable head coil apparatus 100 may have a distance between the base 120 and the extension 140 that is adjustable. At least one of the extension 140 or the base 120 may be releasably coupled to the at least one arm 160. The extension 140 may be movable relative to the base 120 in the anterior/posterior direction. For example, the head coil position may be moveable (1) toward or away from a patient's head and shoulders in a superior to inferior direction, (2) slidable toward or away from a patient's head and shoulders in a direction transverse to the patient's line of bilateral symmetry, and (3) the extension (further discussed below) of the portable head coil apparatus 100 may be movable in a vertical direction relative to the base toward or away from the patient's head or other anatomy.

The portable head coil apparatus 100 may be configured to receive a patient positioning device or apparatus 200 which supports a patient's head. The portable head coil apparatus 100 can be moveable with respect to a patient and a MRI table.

As shown by the embodiment illustrated in FIG. 20, patient positioning device 200 may be configured for use with a patient immobilization device. Nevertheless, the patient positioning device 200 may be a patient immobilization device or any other device or apparatus that can be used to position a patient. Patient positioning device 200 may be configured to transport a patient into the head coil apparatus. Also, the patient positioning device 200 may be used with any type of patient support such as a medical table, a MRI table, a trolley, or any other modality or structure that may support a patient.

The portable head coil apparatus 100 may further include a mirror 150 coupled to and/or attached to the extension. The mirror 150 may act as a feature for positioning the patient relative to the at least one coil array 122 and/or 142 and/or helping to reduce anxiety due to claustrophobia induced by the imaging process. In one embodiment, the mirror 150 is positionally fixed to the extension 140.

The portable head coil apparatus 100 may further include at least one handle 154. The at least one handle 154 may be integrally formed into the base 120. Additionally and/or alternatively, the portable head coil apparatus 100 may have a cable management system 124 integral to the base 120.

In one embodiment, the portable head coil apparatus 100 further comprises at least one feature 152a and/or 152b adapted for aligning the coil with respect to the isocenter of the MRI scanner. The at least one feature 152 may be adapted to be located by a laser positioning system.

According to another aspect of the invention, provided is a patient positioning apparatus 200 configured for positioning within an imaging system. The patient positioning apparatus 200 may comprise: a support structure 210 having a head portion 240 configured such that it defines a space 51 between the head portion 240 of the support structure 210 and the imaging or treatment modality table top.

In accordance with a further aspect of the invention, provided is a patient positioning apparatus 200 configured for positioning within an imaging system. The patient positioning apparatus comprises: a support structure 210 having a head portion 240 adapted to receive a head of a patient and a body portion 220 adapted to receive the body of a patient, the head portion 240 comprising a recess R1 underneath the head portion 240 adapted to receive a MRI coil. The head portion 240 of the support structure 210 may be configured to receive a portable head coil apparatus 100. The patient positioning apparatus 200 may be configured for use in one or more of the imaging or treatment modalities selected from the group consisting of CT, MRI, X-ray, radiation therapy, nuclear therapy, neurosurgery, angiography, stroke treatment, interventional radiology, and interventional cardiology.

The patient positioning apparatus may further include a head support configured to maintain the position of the head of the patient during positioning of the patient. The head support may comprise a low temperature thermoplastic immobilizer. Additionally and/or alternatively, the head support may include pins and/or and a frame. For example, a low temperature thermoplastic immobilizer may be releasably engaged with at least one of the pins and the frame in order to support and/or immobilize the head. Suitable systems and methods for immobilizing a patient are disclosed in U.S. Patent Publication No. 2016/0206395 and U.S. Pat. No. 9,775,934, which are incorporated herein by reference in their entireties for all purposes.

In accordance with yet another aspect of the invention, a coil positioning system 300 is provided. The coil positioning system 300 comprises a portable head coil apparatus 100 configured to be moveable to a patient and to receive a portion of a patient positioning apparatus. The portable head coil apparatus 100 may include: a base 120 comprising at least one coil array 122, the base 120 being positionable to facilitate imaging by the at least one coil array 122, an extension 140 comprising at least one coil array 142, the extension 140 being spaced from the base 120 by a distance d1, and an arm 160 coupled to the base 120 and the extension 140, the at least one coil array 122 of the base 120 and the at least one coil array 142 of the extension 140 defining an imaging region 126 therebetween, the imaging region 126 having a cross-sectional area that is adjustable for facilitate imaging by the at least one coil array 142 of the extension 140 and the at least coil array 122 of the base 120. The coil positioning system 300 further comprises a patient positioning apparatus 200 having a support structure 210. The patient positioning apparatus 200 may include: a head portion 240 adapted to receive a head of a patient, the head portion 240 having a length L2 and a thickness t2, and a body portion 220 adapted to receive the body of a patient, the body portion 220 having a length L1 and a thickness t1. The thickness t1 of the body portion 220 may be greater than the thickness t2 of the head portion 240, such that the head portion 240 at least partially defines a space 51 into which a portion of the base 120 of the portable head coil apparatus 100 is received.

The coil positioning system 300 may be configured such that in an imaging position, one of the base 120 or the extension 140 is positioned posterior to the head of the patient and the other of the base 120 or the extension 140 is positioned anterior to the head of the patient. Additionally and/or alternatively, the coil positioning system 300 may be configured such that in the imaging position, the portion of the base 120 of the portable head coil apparatus 100 extends into the space at least partially defined by the head portion 240 of the patient positioning apparatus 200.

According to yet a further aspect of the invention, provided is an imaging system 400. The imaging system 400 comprises: a portable head coil apparatus 100 configured to be moveable to a patient and to receive a portion of a patient positioning apparatus 200; a patient positioning apparatus 200 having a support structure 210; and an imaging scanner 410. The portable head coil apparatus 100 may include: a base 120 comprising a first coil array 122, the base 120 being positionable to facilitate imaging by the first coil array 122; an extension 140 comprising a second coil array 142, the extension 140 being spaced from the base 120 by a distance d1; and an arm 160 coupled to the base 120 and the extension 140, the first coil array 122 and the second coil array 142 defining an imaging region 126 therebetween. The patient positioning apparatus 200 may include a head portion 240 adapted to receive a head of a patient, the head portion 240 having a length L2 and a thickness t2, and a body portion 220 adapted to receive the body of a patient, the body portion 220 having a length L1 and a thickness t1. The thickness t1 of the body portion 220 may be greater than the thickness t2 of the head portion 240. The imaging system 400 may further have a laser system 420 configured for to identify a location of a feature 152 disposed on the portable head coil apparatus 100.

In accordance with yet another aspect, a method is provided for positioning a portable head coil apparatus 100 relative to a patient for imaging. The method comprises positioning a base 120 including a first coil array 122 to facilitate imaging of the patient by the first coil array 122 by moving the base 120 in a positioning direction; positioning an extension 140 including a second coil array 142 to facilitate imaging of the patient by the second coil array 142 by moving the extension 140 relative to the base 120 along an extending direction, thereby at least partially defining an imaging region 126 for receiving a body part of a patient to be imaged, the extending direction being orthogonal to the positioning direction; and retaining a selected distance between the first coil array 122 and the second coil array 142 along the extending direction, thereby maintaining the size of the imaging region 126 at least partially defined by the extension 140 and the base 120. The method may further include positioning the base 120 and the extension 140 relative to a patient positioning apparatus. For example, the method may include positioning the base 120 and the extension 140 such that the head of the patient extends into the imaging region 126 defined by the base 120 and the extension 140. Additionally and/or alternatively, the method includes positioning the patient positioning apparatus 200, the base 120, and the extension 140 at least partially into an imaging scanner 410. In one embodiment, the method also includes aligning the patient positioning apparatus 200, the base 120, and the extension 140 relative to the imaging scanner 410 using a laser positioning system 420.

Figure 33:
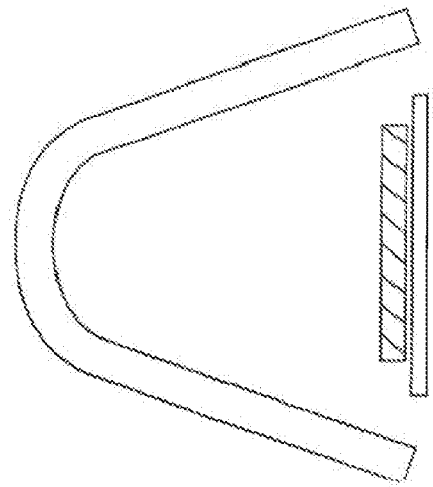
FIG. 33 is a cross-sectional view of a further coil apparatus and a patient positioning apparatus according to aspects of the invention.
Figure 32:
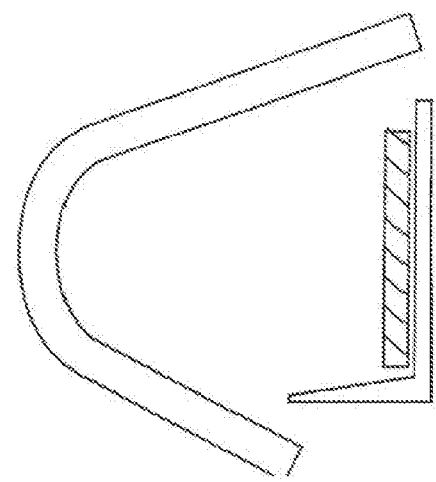
FIG. 32 is a cross-sectional view of another coil apparatus and a patient positioning apparatus in accordance with aspects of the invention.
Figure 31:
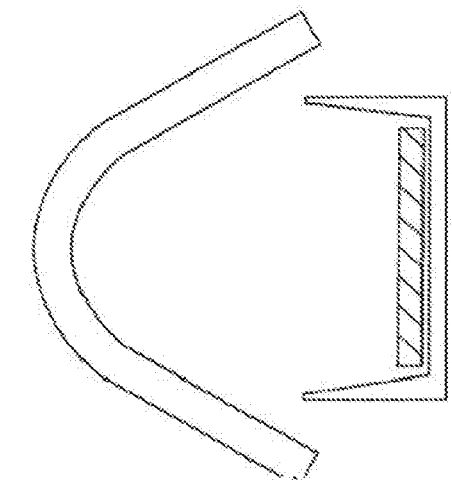
FIG. 31 is a cross-sectional view of a coil apparatus and a patient positioning apparatus according to aspects of the invention.
Figure 35:
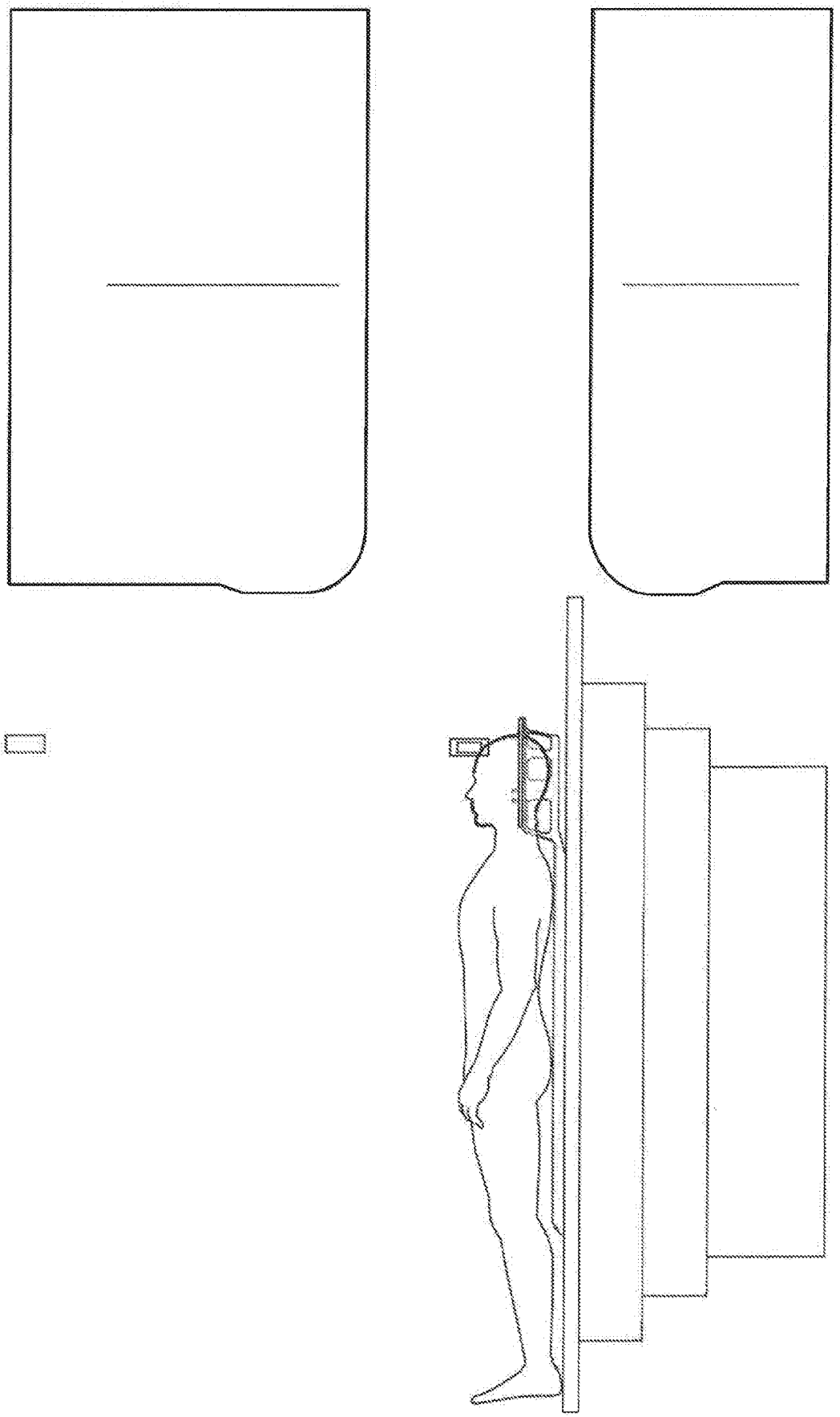
Figure 36:
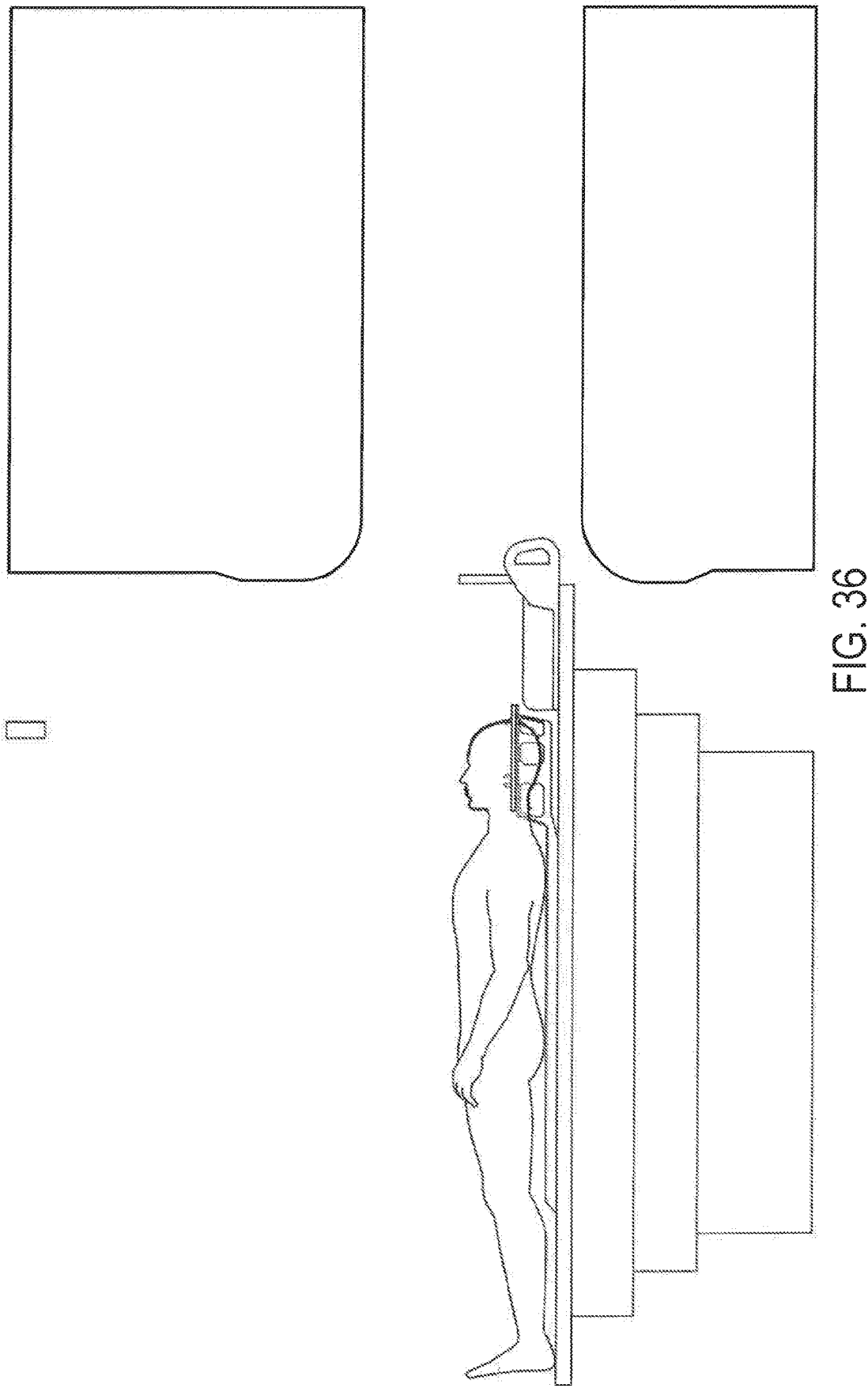
Figure 37:
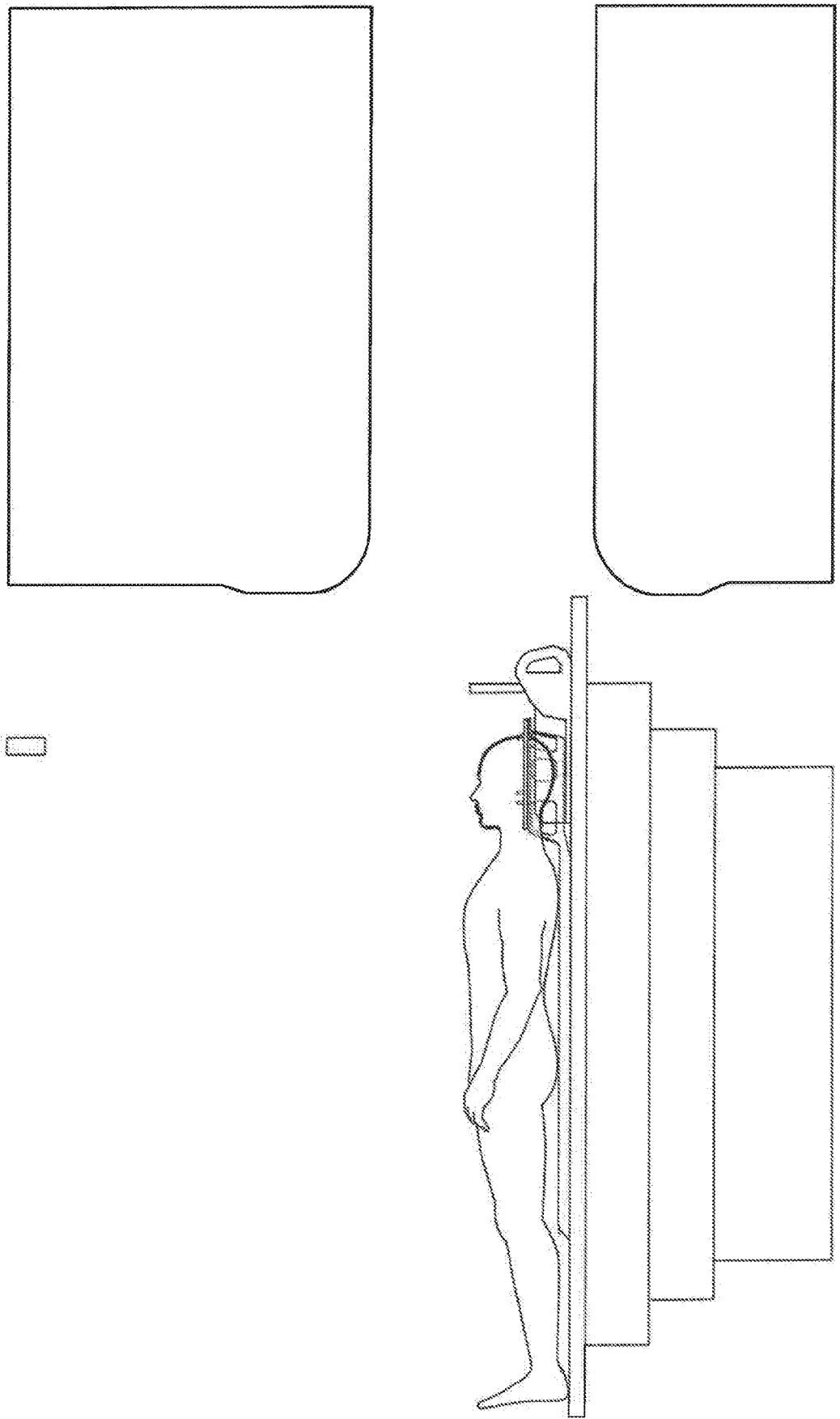
Figure 38:
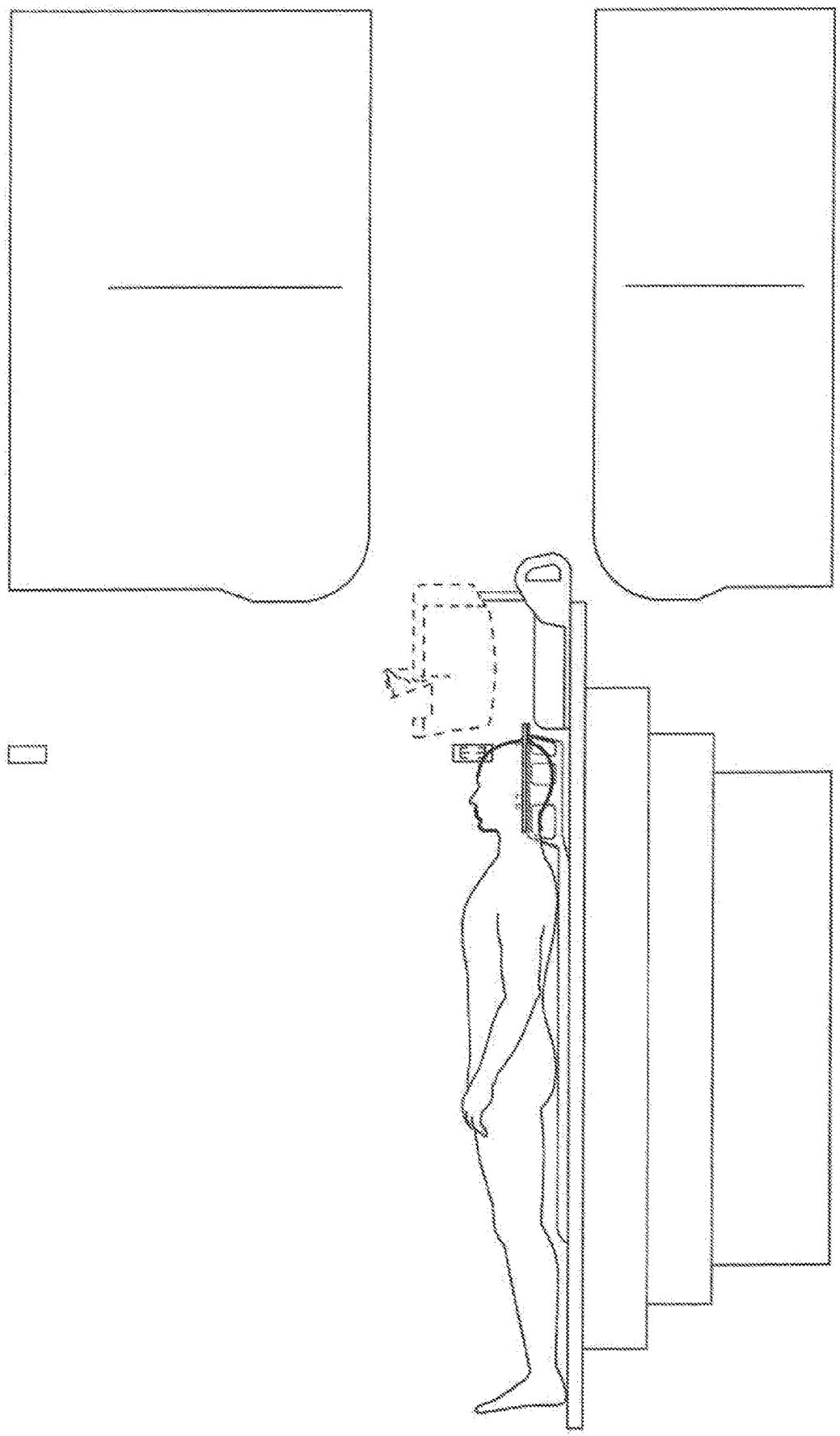
Figure 40:
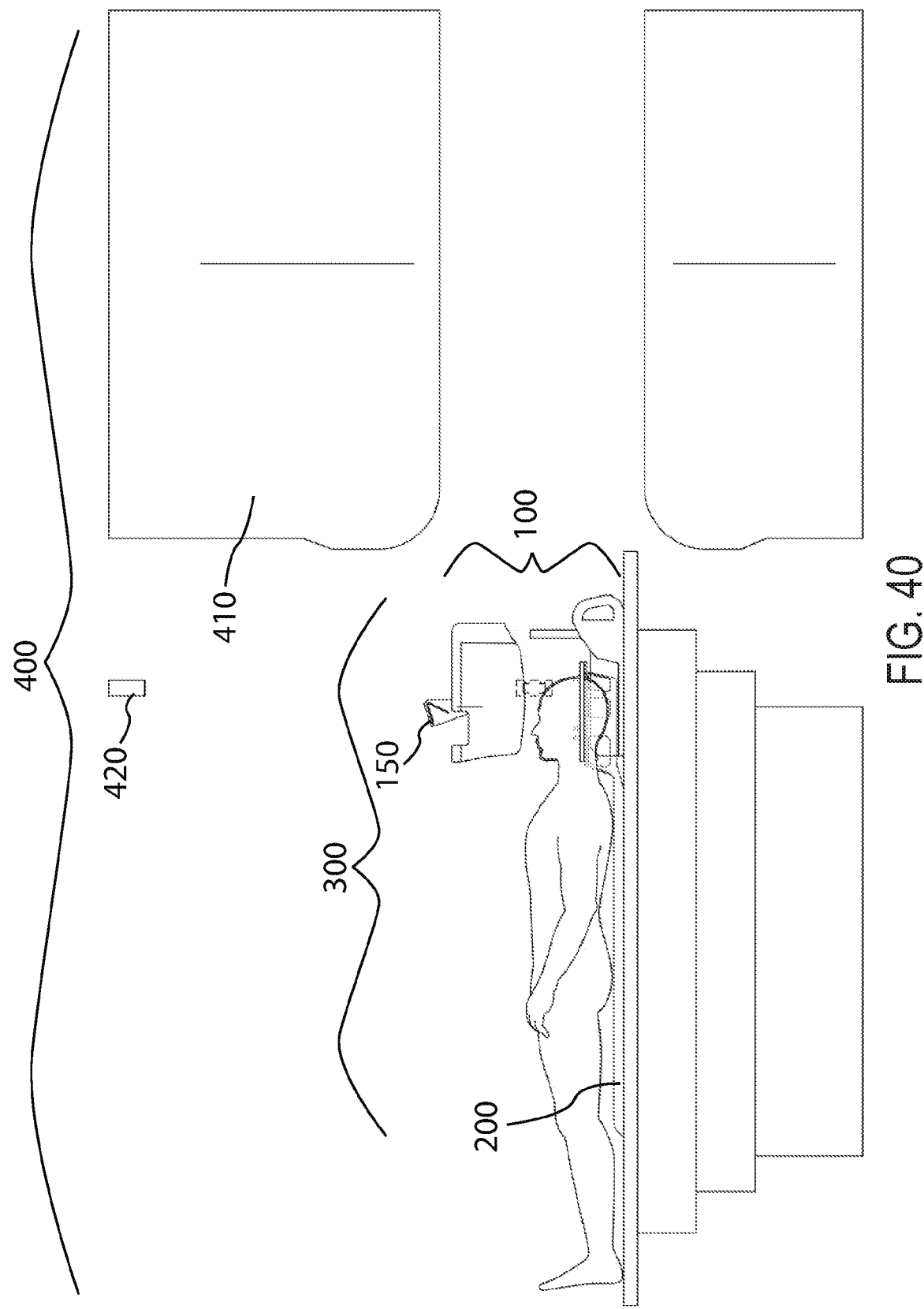
Figure 41:
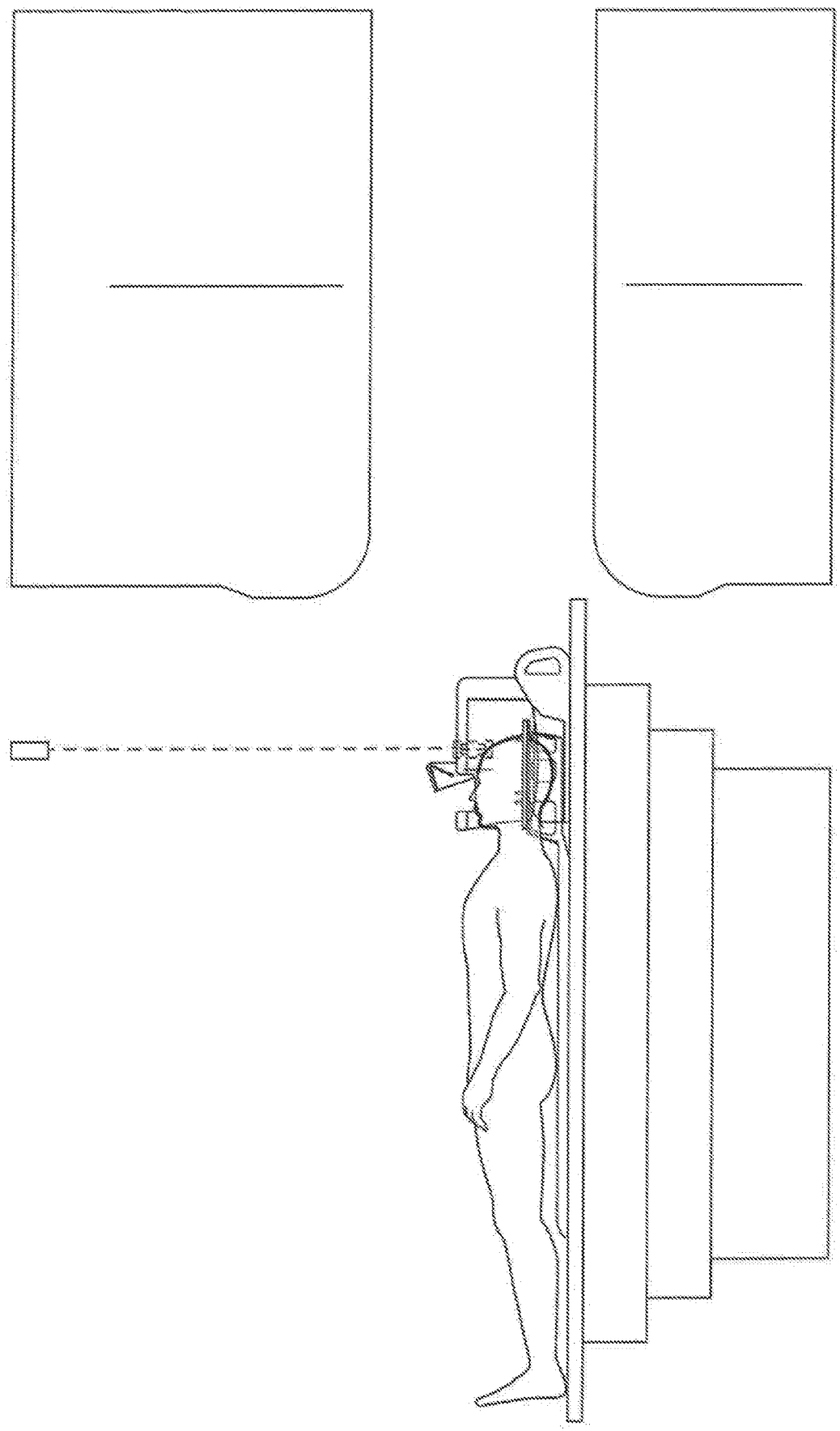
Figure 42:
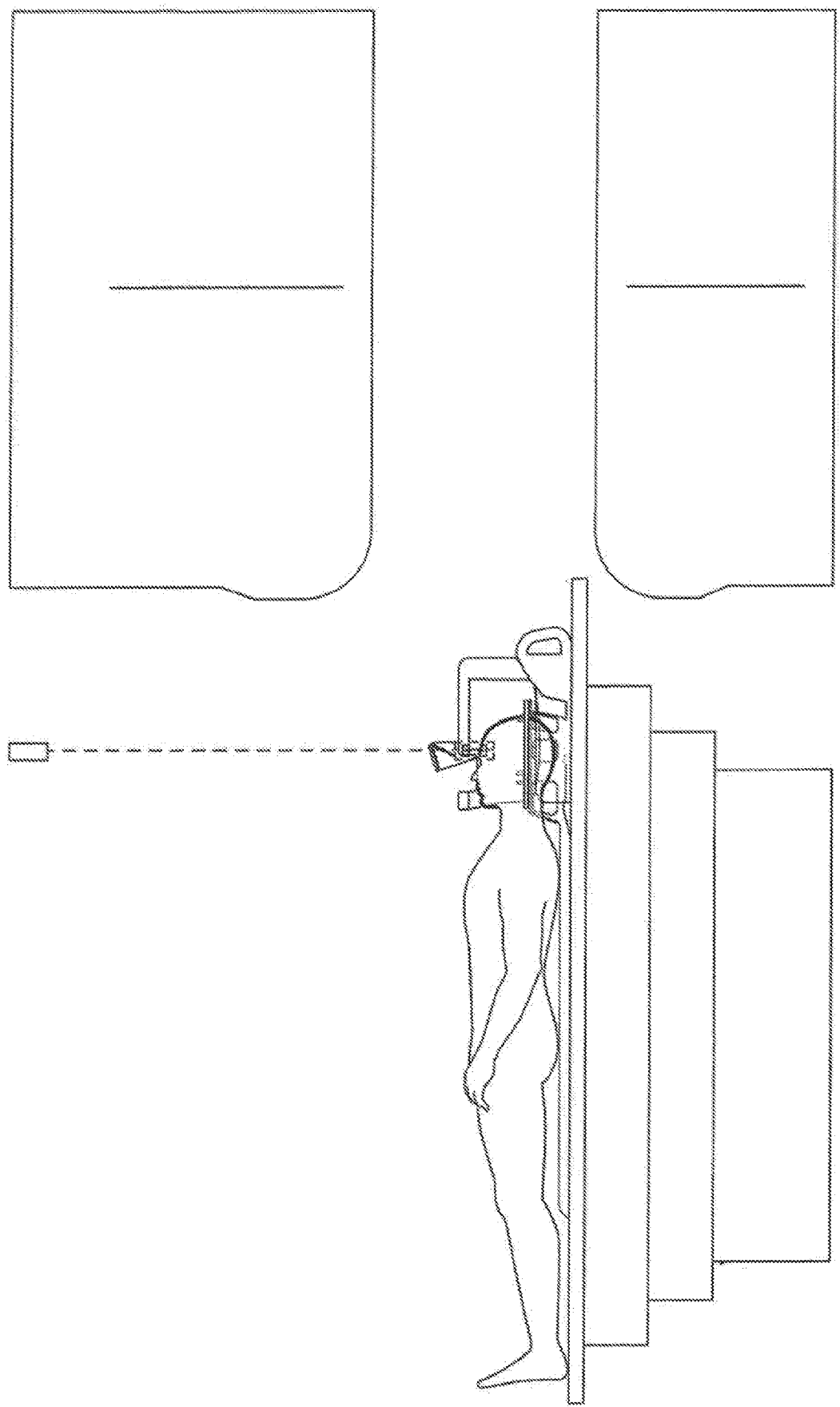
Figure 43:
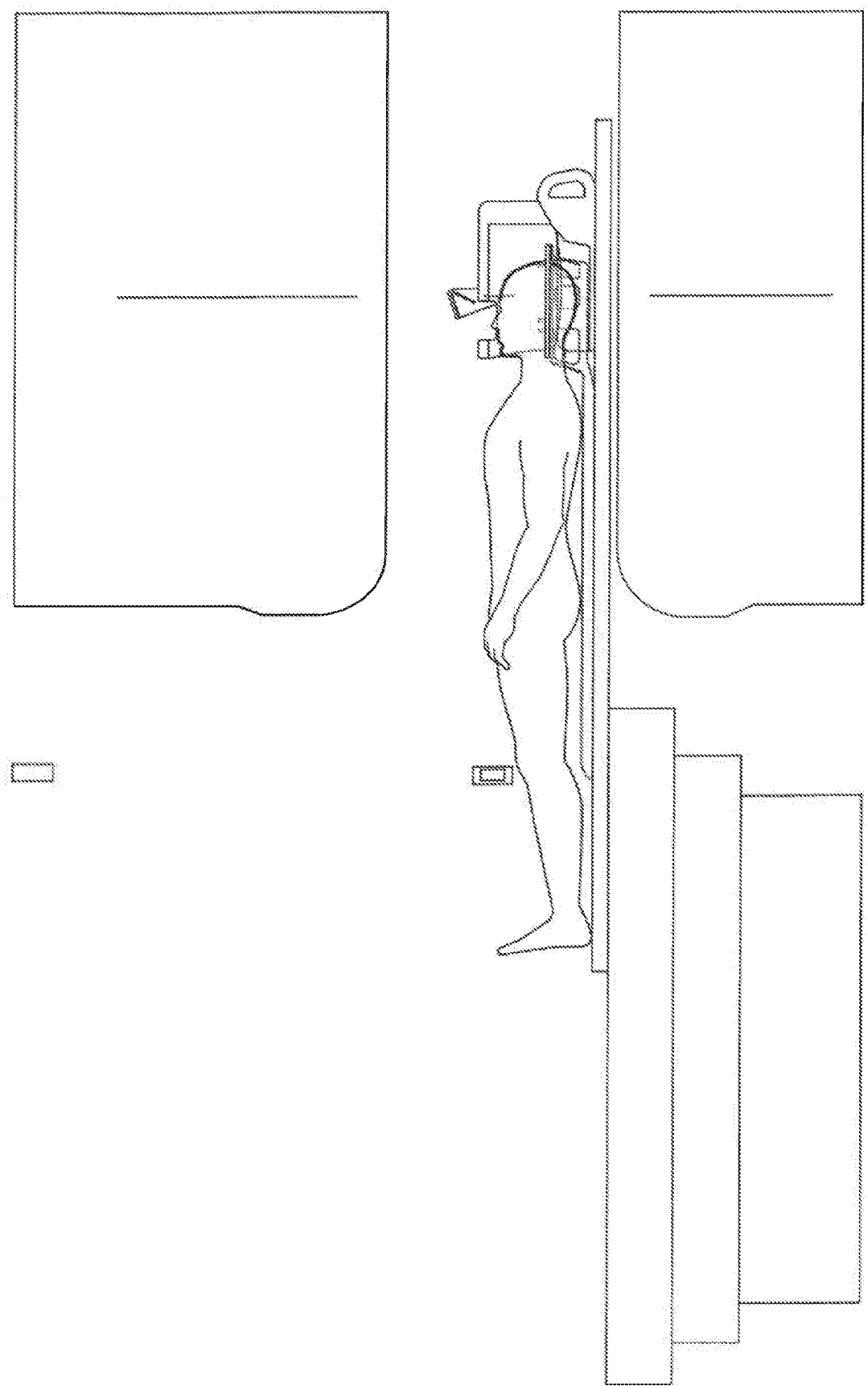

FIGS. 31 to 33 generally illustrate various embodiments in which the configurations of the extension and/or the base are modified. FIG. 40 illustrates a first of such embodiments of a head coil system 300. Head coil system 300 includes features that are similar to the features of portable head coil apparatus 100 and patient positioning device 200 and, thus, similar reference numbers and/or terms are used to refer to similar features. Additionally, discussions of one or more features of head coil system 300 may be omitted if such features are disclosed with reference to other embodiments of the invention. A more detailed description of the portable head coil apparatus 100 illustrated in FIGS. 1-14 and 44-46B is now provided below.

Portable head coil apparatus 100 is preferably configured for unrestricted movement relative to a patient's head supported by a patient positioning device, such that portable head coil apparatus 100 may be moveable toward or away from a patient's head in superior to inferior direction or lateral direction. For example, head coil apparatus 100 may be configured to have unrestricted movement that further includes the ability to rotate the portable head coil apparatus 100 about an axis perpendicular to the patient table. In one embodiment, the head coil apparatus may be configured to have unrestricted movement that further includes movement in any direction, such that portable head coil apparatus 100 has motion in all degrees of freedom. The extent of the movement of the head coil apparatus may be limited by, e.g., a power cord, a cable attachment, cable management system 124 or the like.

Figure 46A:
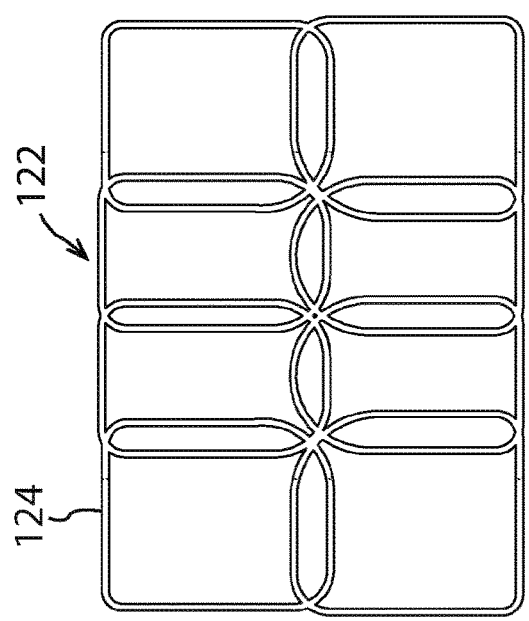
FIG. 46A is a view of the coil array of the base of the portable head coil apparatus of FIG. 44.
Figure 46B:
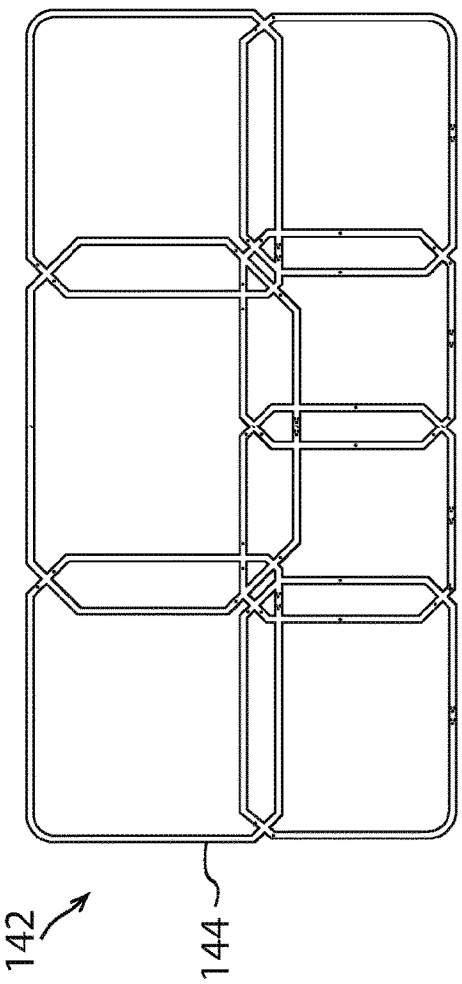
FIG. 46B is a view of the coil array of the extension of the portable head coil apparatus of FIG. 44.
Figure 47D:
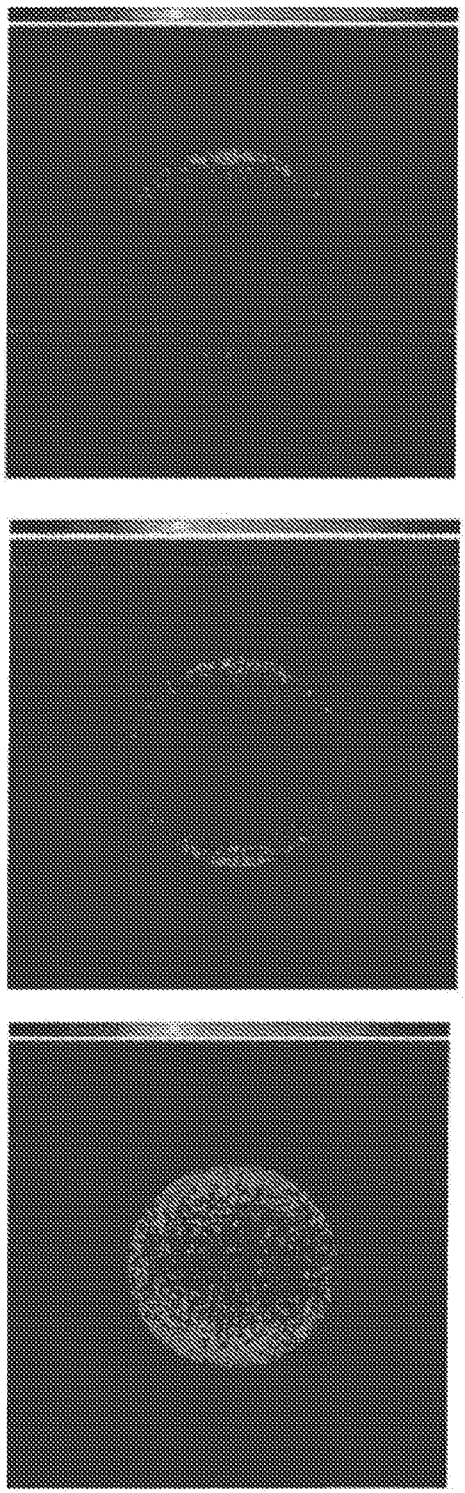
Figure 47E:
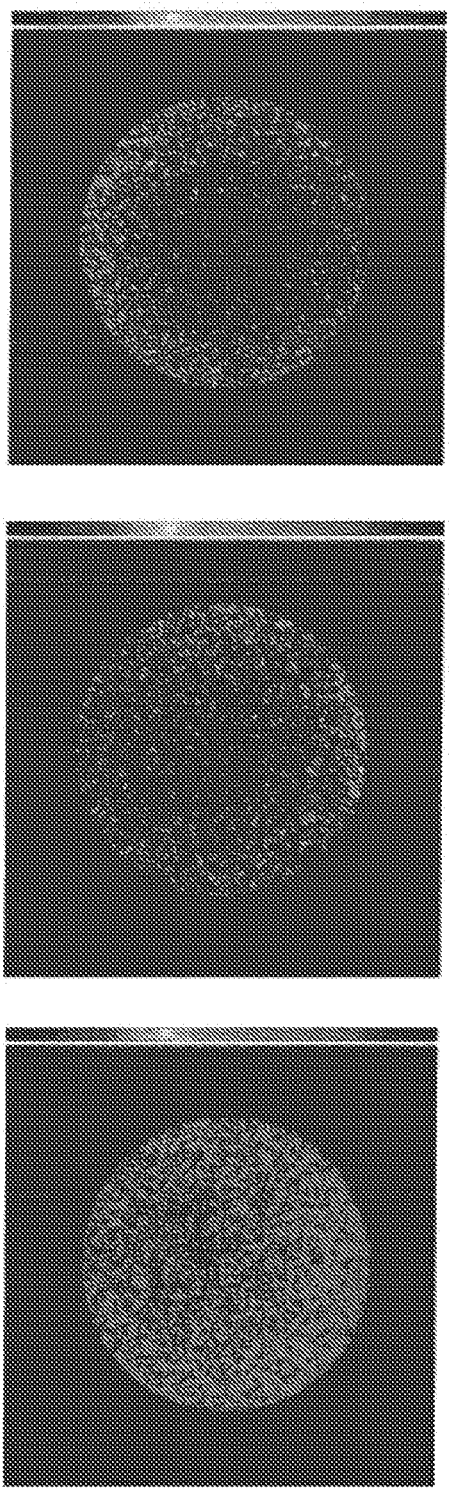

As previously mentioned, portable head coil apparatus 100 includes a base 120, an extension 140, and an arm 160 coupled to base 120 and extension 140. Base 120 is configured to be positionable relative to a patient's head. Base 120 includes at least one coil array 122 comprising at least two coil elements 124. Coil array 122 is contained within at least one housing 123 defined by base 120. Coil array 122 is comprised of at least two coil elements 124. As illustrated in FIG. 46A, coil array 122 may be formed of eight coil elements 124. Coil array 122 may be formed of an electrically conductive material positioned on a flexible substrate according to known methods of manufacturing.

Figure 6:
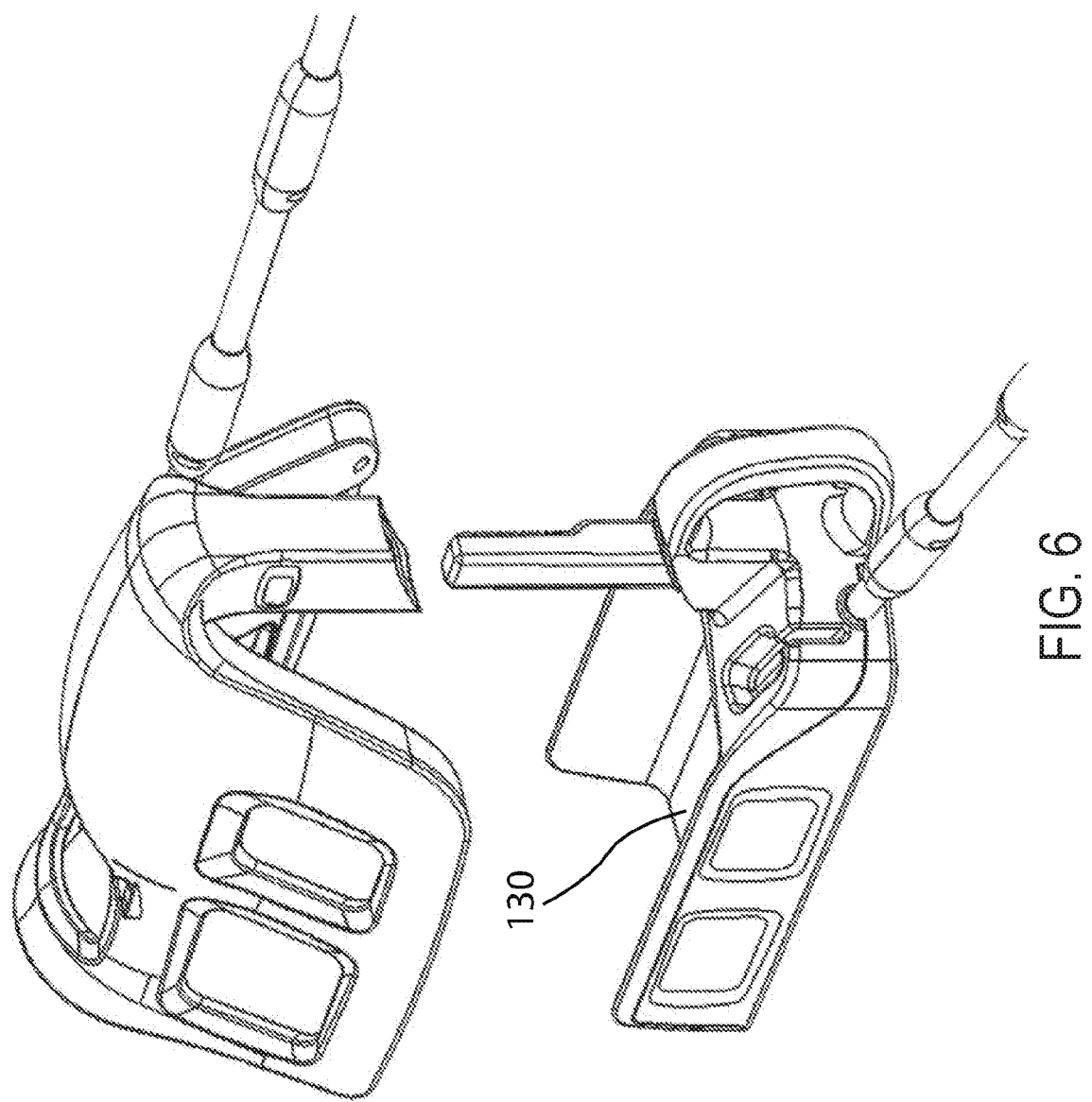
Figure 7:
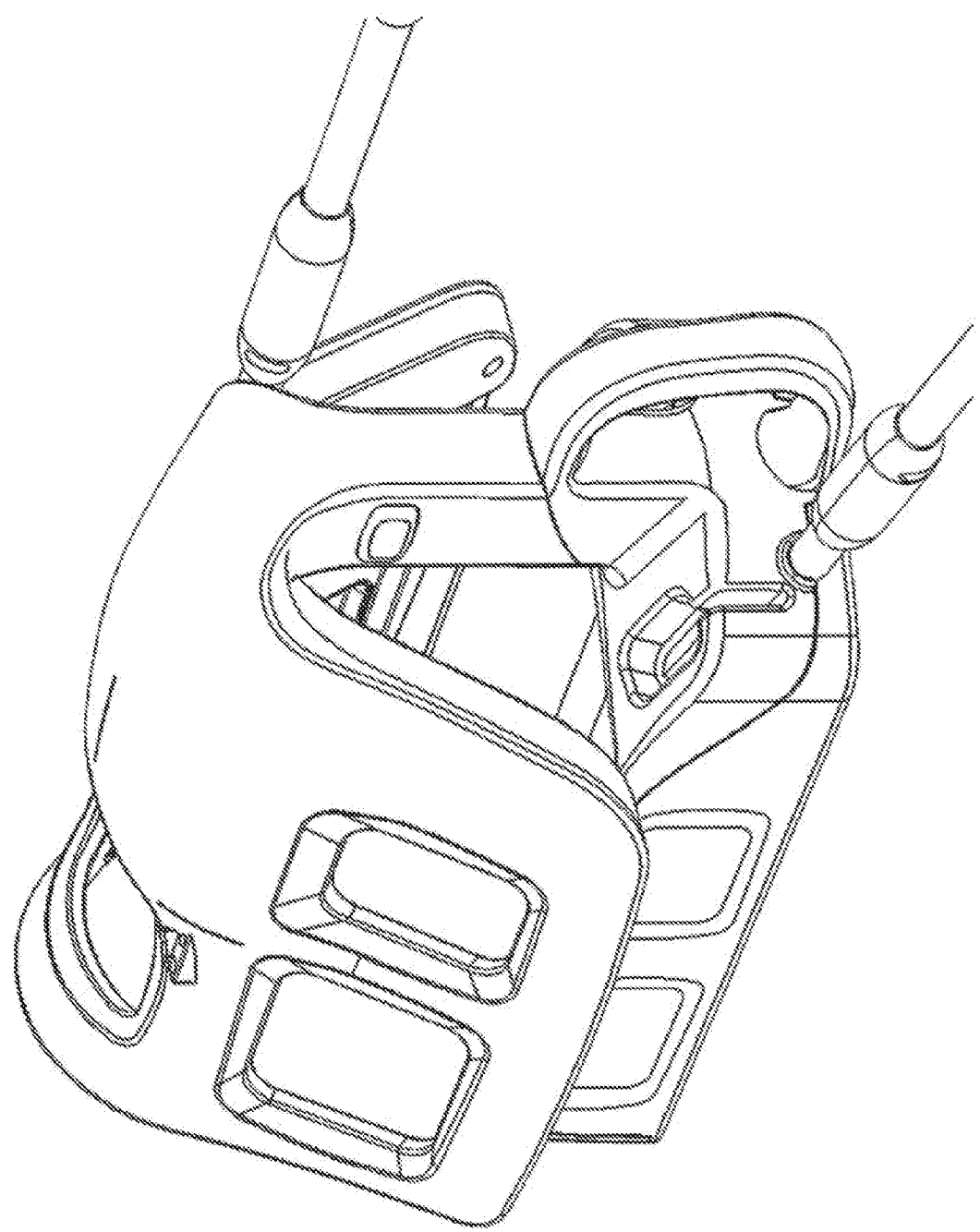
Figure 8:
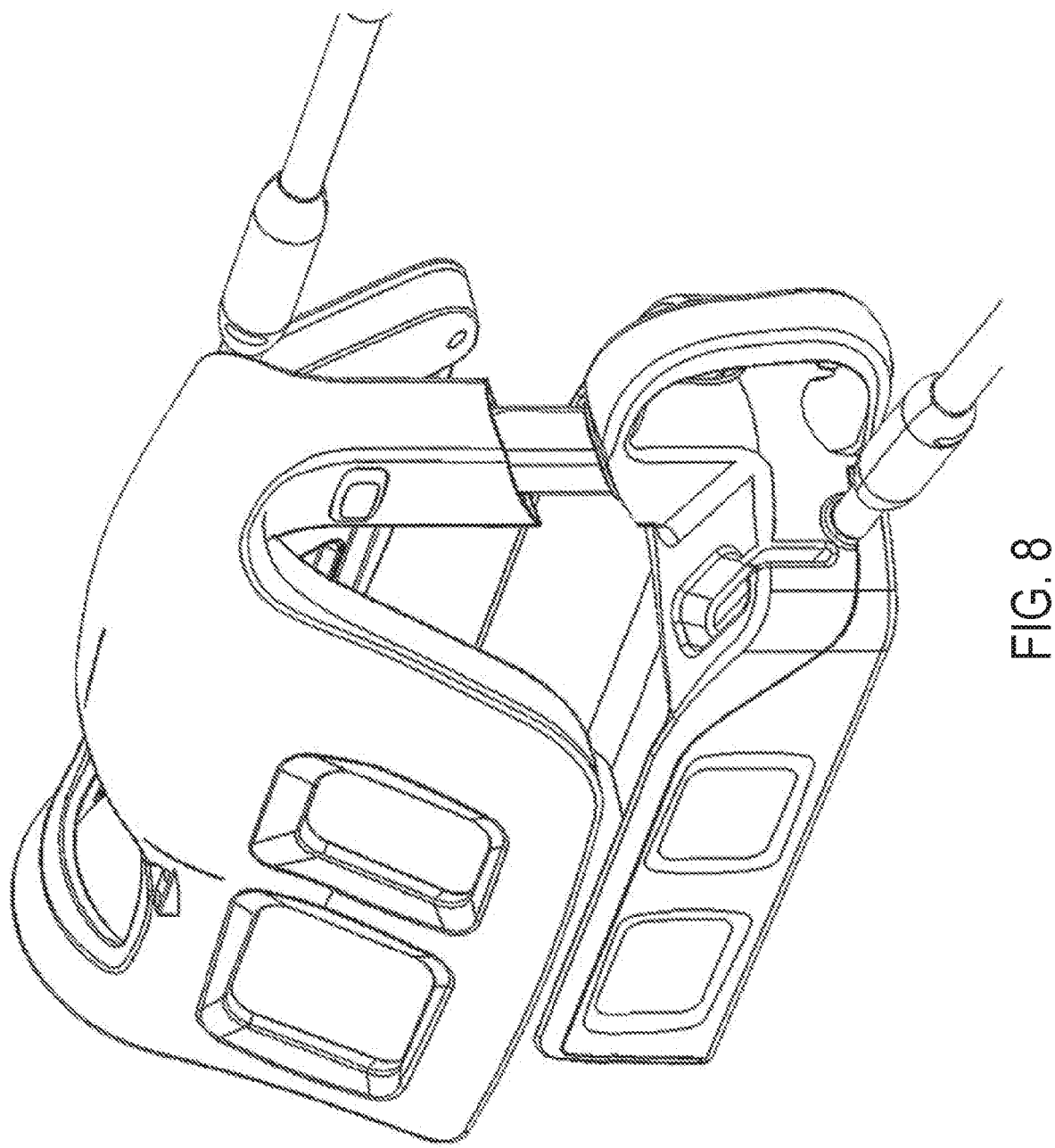
Figure 9:
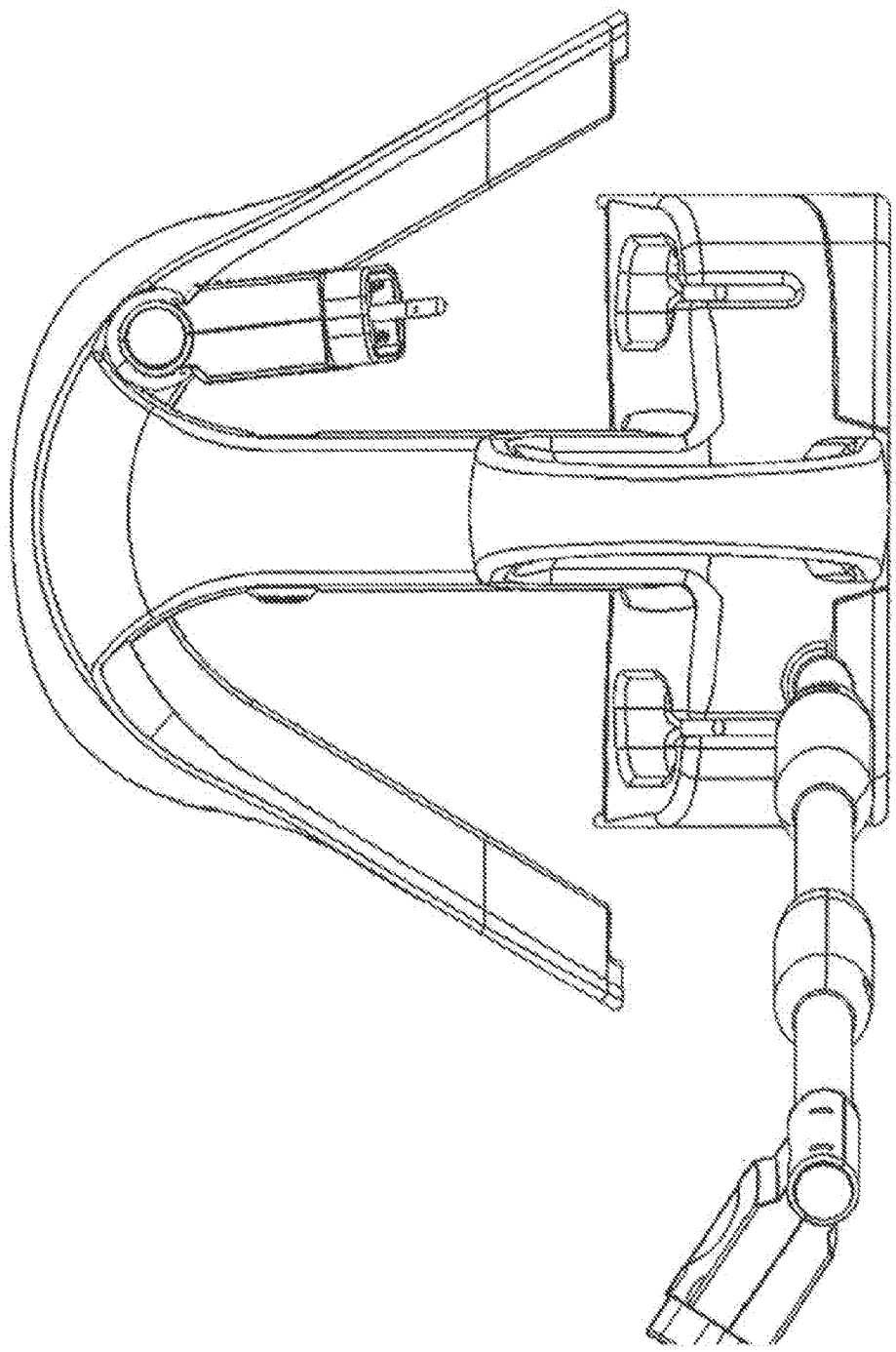
Figure 10:
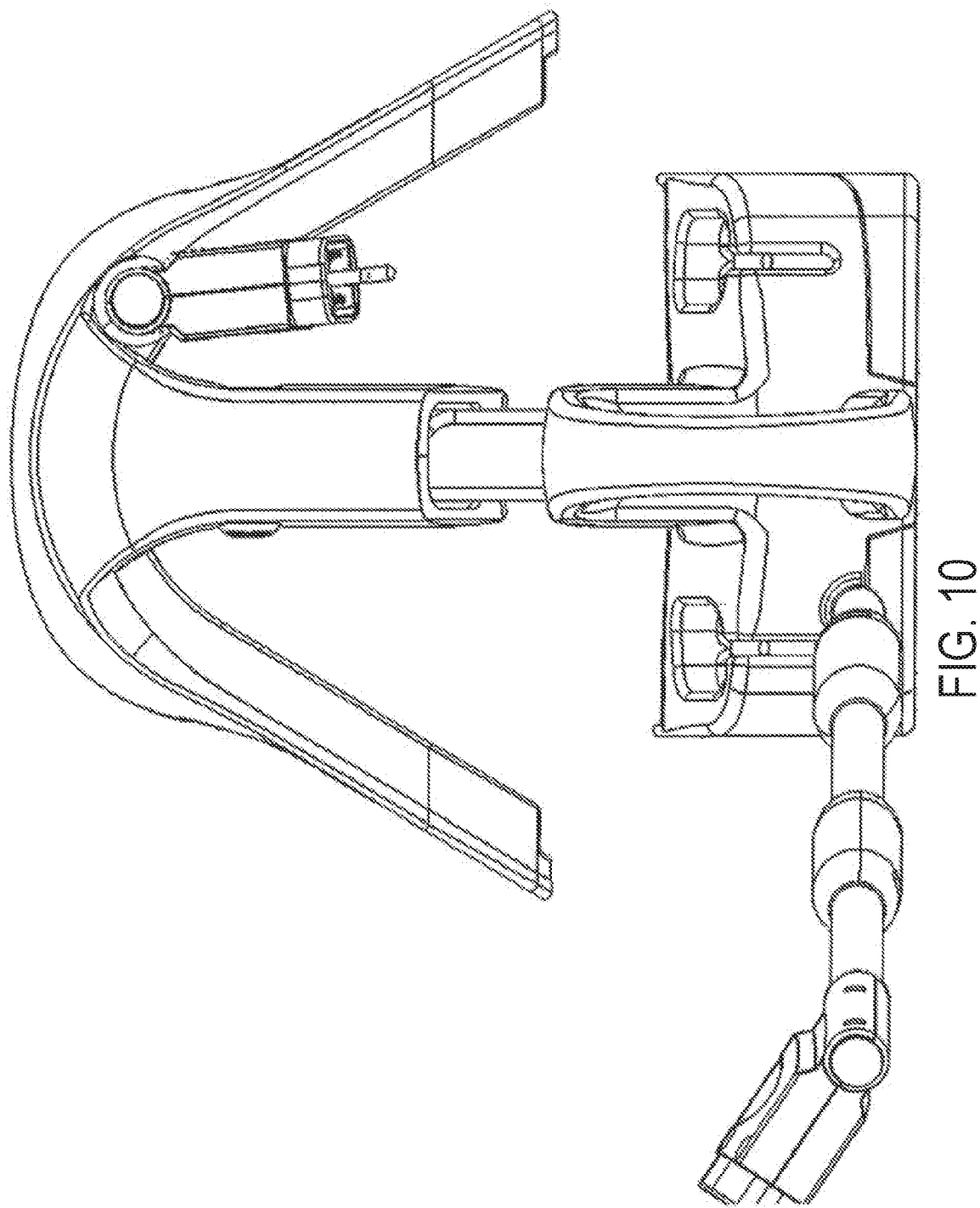
Figure 11:
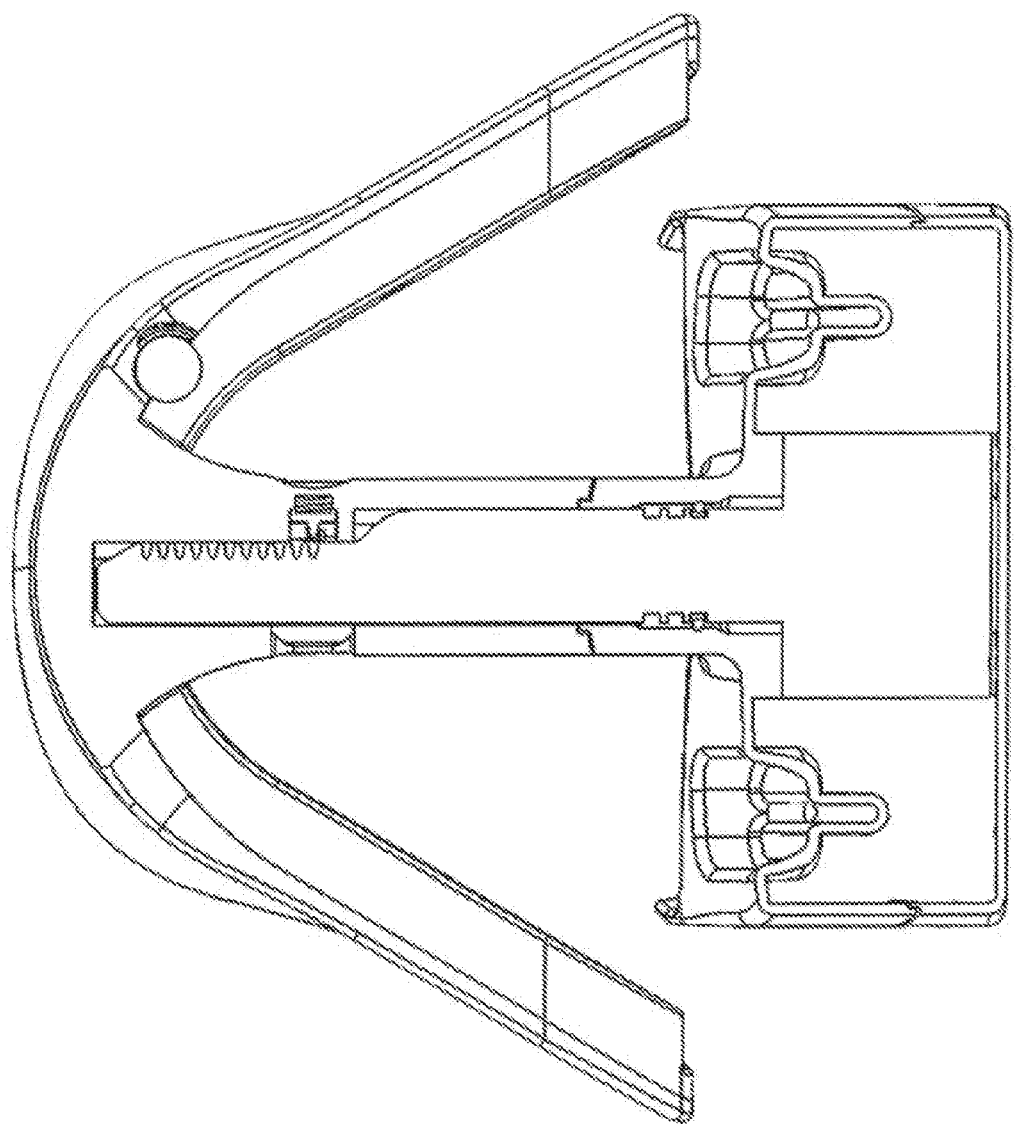
FIGS. 11-14 are cross-sectional views of the head coil apparatus of FIG. 1.
Figure 12:
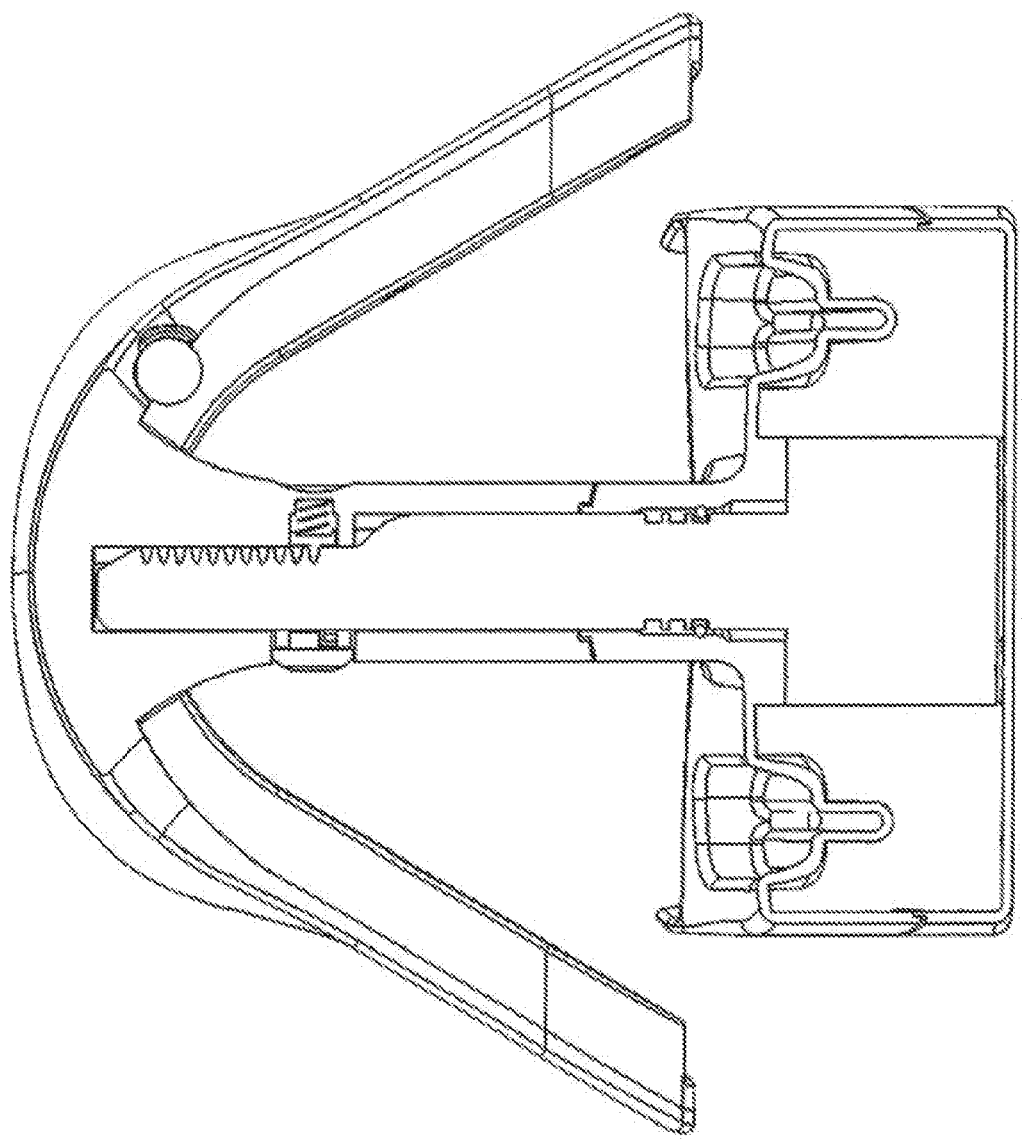
Figure 13:
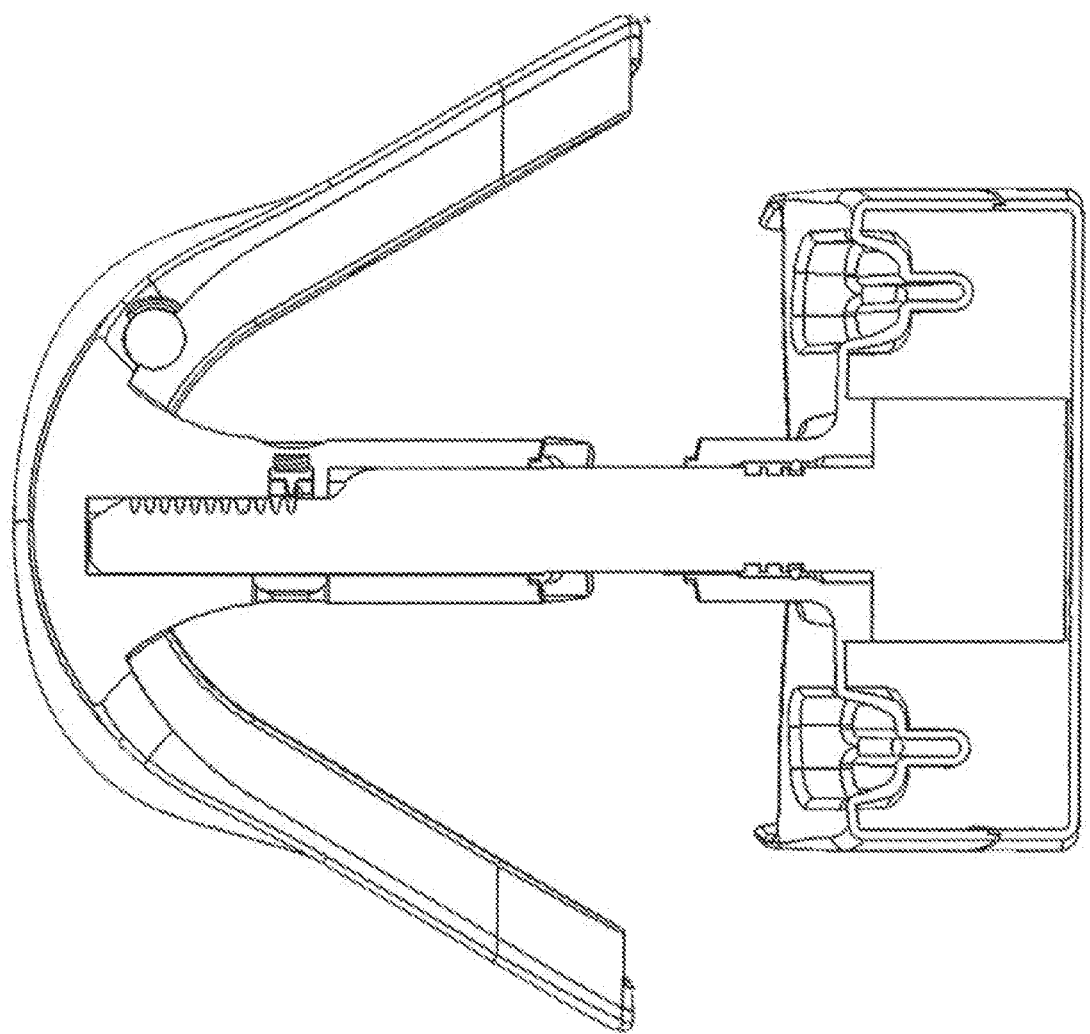
Figure 44:
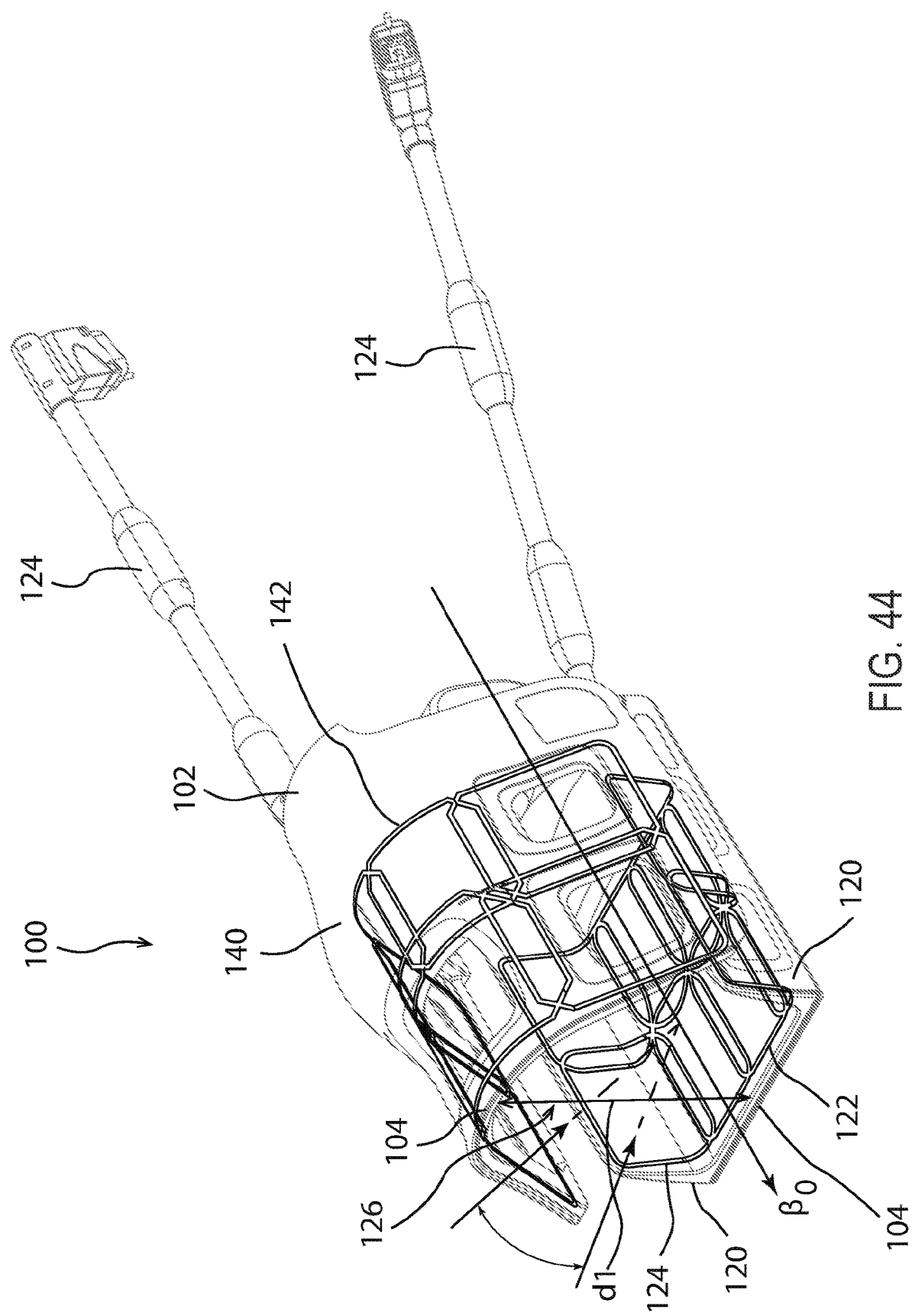
FIG. 44 is a perspective view of a portable head coil apparatus in accordance with an aspect of the invention with the surface of the extension and base being illustrated as semi-transparent to better illustrate the coil array.
Figure 45:
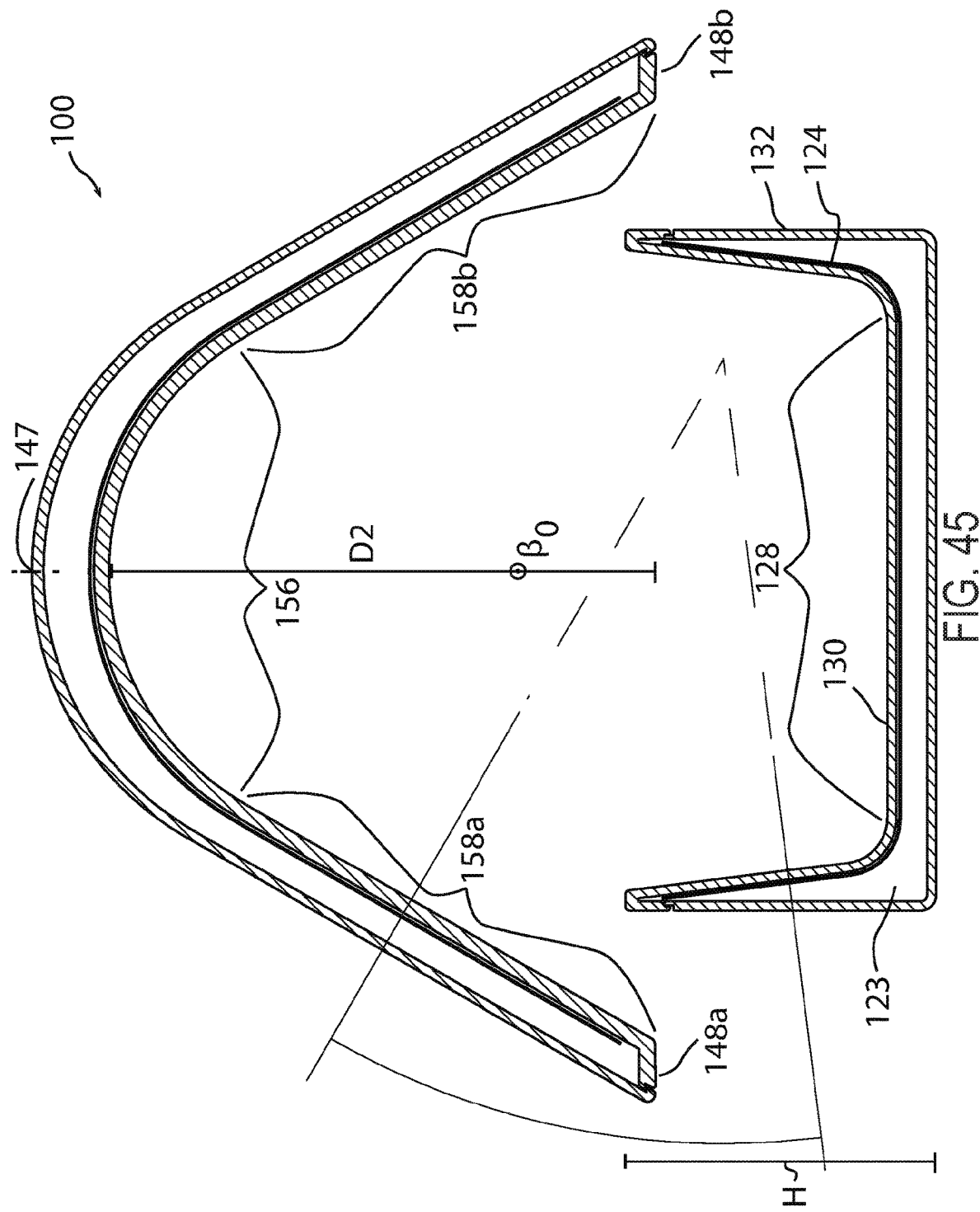
FIG. 45 is a cross-sectional view of the portable head coil apparatus of FIG. 44.

Referring to FIGS. 6 and 45, base 120 has a receiving portion 128 that includes a receiving surface 130. Receiving surface 130 may form a curvature or may be flat or substantially flat. As illustrated in FIGS. 1-14, 44, and 45, base 120 includes receiving portion 128 having a receiving surface 120 that is substantially flat and, thus, defines an insignificant or negligible curvature. In one embodiment, receiving surface 120 is flat as to extend along a plane. Although not shown in the illustrated embodiment, receiving surface 130 may include one or more grooves or protrusions, e.g., for engaging and/or facilitating alignment of portable head coil apparatus 100 with a patient positioning device. Alternatively, base 120 may have a uniform thickness across receiving portion 128.

Base 120 may include one or more side walls 132 that extend from receiving portion 128. For example, base 120 may include solely one side wall 132 as illustrated in FIG. 32 or may include two side walls as illustrated in FIGS. 31, 44, and 45. In addition, base 120 may be configured without sidewalls, i.e., with zero side walls, as illustrated in FIG. 33. Side walls 132 and receiving portion 128 may be integrally formed as one item and/or configured to together form a single housing 123. One or more coil elements 124 of coil array 122 may positioned within a section of housing 123 defined by side walls 132. In one embodiment, only a portion of the coil elements 124 is positioned within the section of housing 123 defined by side walls 132. Side walls 132 may be configured to align a head portion of a positioning device with portable head coil apparatus 100. Additionally, portable head coil apparatus 100 may include a first side wall and a second side wall that extend upward from receiving portion 128 in a parallel or substantially parallel direction.

Extension 140 is configured to be movable relative to base 120 and includes at least one coil array 142 comprising at least two coil elements 144. Coil array 142 is contained within at least one housing 143 at least partially defined by extension 140. Although extension 140 is illustrated in FIG. 45 as defining a single housing 143 containing a single coil array 142, in another embodiment extension 140 defines a plurality of housings 123 that contain at least a portion of coil array 142. In one embodiment, portable head coil apparatus 100 contains only two housings for containing coil arrays (e.g., a single housing 123 for base 120 and a single housing 143 for extension 140). Additionally, coil array housings 123 and 143 may each contain a single coil array (e.g., coil array 122 and coil array 144, respectively).

Inner surface 146 defines a curvature extending along inner surface 146, e.g., from a first side end 148a to a second side end 148b. In one embodiment, a continuous curvature is defined along the entire inner surface 146 of extension 140 from first side end 148a to second side end 148b. In another embodiment, however, inner surface 146 defines a curvature extending across center 147 of extension 140. Inner surface 146 may be configured to define a plurality of different curvatures or planes corresponding to sections of inner surface 146. For example, the curvature defined by inner surface 146 may have a parabolic shape or substantially parabolic shape at a center section 156 or across the entire inner surface 146. By way of another example, inner surface 146 may define a continuous curvature extending along a center section 156 of inner surface 146 while defining a plane or different curvature extending along first side section 158a and second side section 158b of inner surface 146. Inner surface 146 of extension 140 may also define a concavity. The concavity defined by inner surface 146 may have a maximum depth D2, e.g., at center 147, that is greater than height H of base 120, which includes side walls 132, if any.

Inner surface 146 of extension 140 and receiving surface 130 of base 120 together at least partially define imaging region 126 therebetween for receiving a patient's head supported on a patient positioning device. Imaging region 126 extends from a superior end 102 of portable head coil apparatus 100 to an inferior end 104 of portable head coil apparatus 100 and is, preferably, accessible from both the superior end 102 and the inferior end 104 of portable head coil apparatus 100. For example, imaging region 126 may be accessible to a patient's head from inferior end 104, while imaging region 126 may be accessible to a doctor's hand from superior end 102.

Additionally, extension 140 may include an opening adapted to align coil array 122 of base 120 and coil array 142 of extension 140 with the region of interest. The opening of the extension may also be suitable to permit the patient to see outside of the confines of the portable coil apparatus in order to alleviate patient anxiety. The opening may be sized, based on the $95^{th}$ percentile of adult patient's faces, to extend from a forehead of a patient to an upper lip region of the patient and from a first side of the patient's face to a second side of a patient's face.

Arm 160 is coupled to base 120 and extension 140 and is configured to space base 120 from extension 140 and to adjust the position of extension 140 relative to base 120 between an extended position in which the extension is spaced from base 120 and an imaging position in which extension 140 is closer (e.g., adjacent) to base 120. Arm 160 may be releasably coupled to at least one of base 120 and extension 140, such that extension 140 may be decoupled from base 120. In one embodiment, extension 140 may be decoupled and removed from base 120, such that extension 140 has unrestricted movement when decoupled and/or removed from base 120. Enabling extension 140 to have unrestricted movement after being removed from base 120 is highly advantageous in medical settings where complete access to the patient or removal of the patient from a head coil device in an expedient manner may be critical to the patient's safety. The unrestricted movement of extension 140 is also advantageous as it permits the clinician a variety of options in positioning the coil and the patient with any positioning devices relative to one another. The clinician may set the base down, set the patient positioning device in place, put the patient in the patient positioning device, and then put extension 140 in place, adjusting the position of extension 140 as appropriate to form the imaging region. Alternately the clinician may position the patient in the patient positioning device and then slide base 120 (whether independently from extension 140 as in the previous example or as part of the complete portable head coil apparatus 100) into the recessed portion of the patient positioning device suited to receive portable head coil apparatus 100. Essentially, the unrestricted movement of the portable head coil apparatus 100 enables the clinician the option to either move/position portable head coil apparatus 100 into place relative to the patient and the positioning device or to move/position the patient and positioning device relative to the coil arrays 122 and/or 142 of portable head coil apparatus 100.

Arm 160 may adjust the distance of extension 140 from base 120, e.g. using a ratchet mechanism 170 configured to secure extension 140 at a distance from base 120. Arm 160 may also include a quick release button 168 configured for releasing and/or decoupling of extension 140 from base 120. Quick release button 168 may be spring based and is, preferably, positioned such that a user can activate quick release button 168 with a single finger while gripping arm 160 with the same hand.

Figure 14:
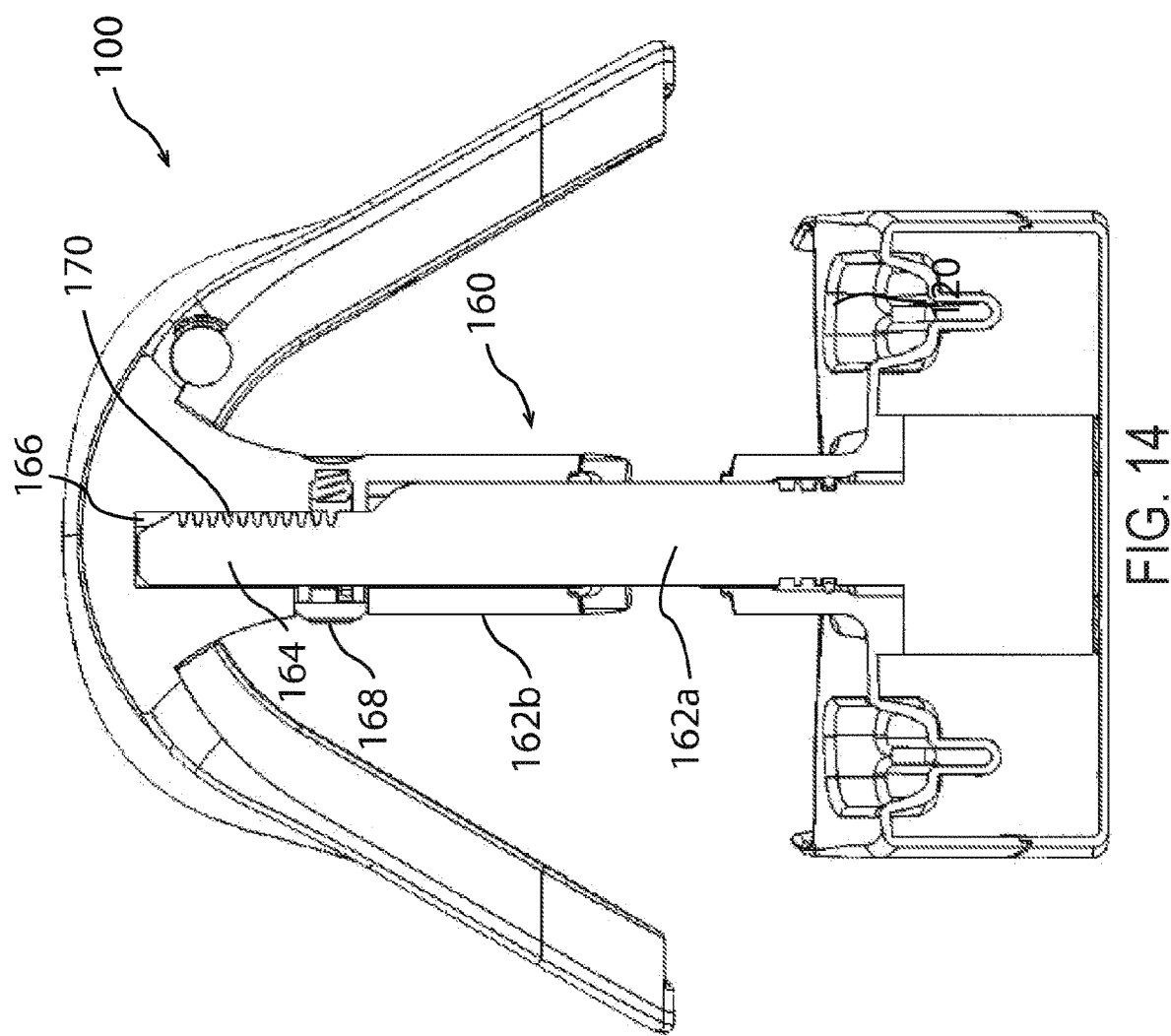
Figure 15:
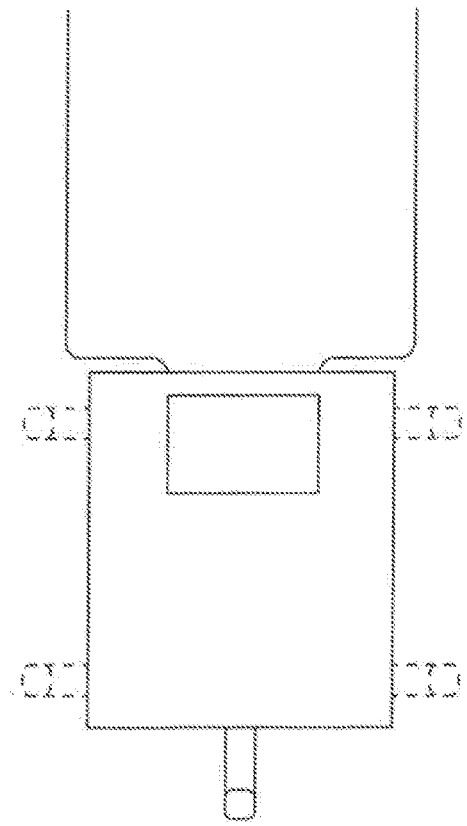
FIGS. 15-17 are top and cross-sectional views of a second embodiment of a coil apparatus according to aspects of the invention.
Figure 16:
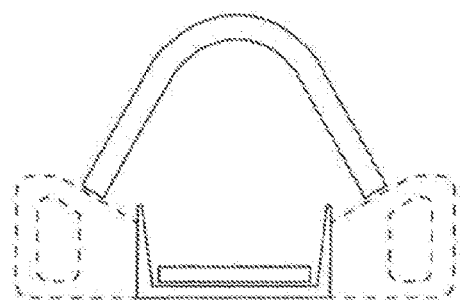
Figure 17:
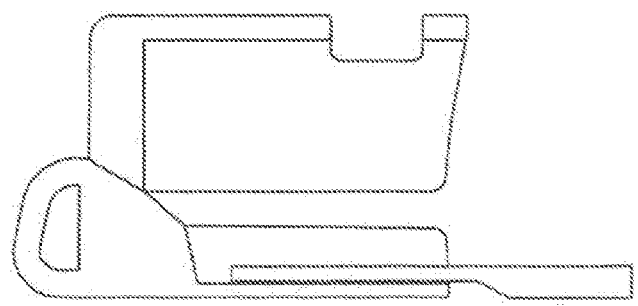
Figure 18:
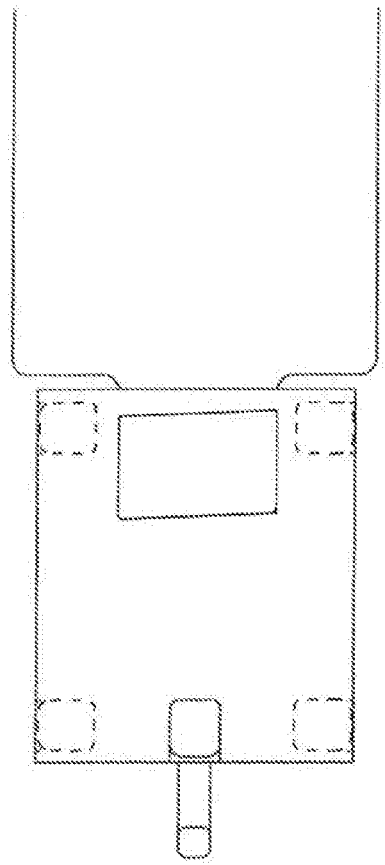
FIGS. 18-19B are top and cross-sectional views of a third embodiment of a coil apparatus in accordance with aspects of the invention.
Figure 19A:
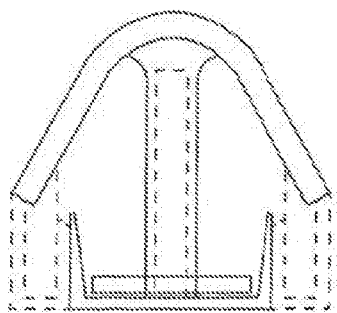
Figure 19B:
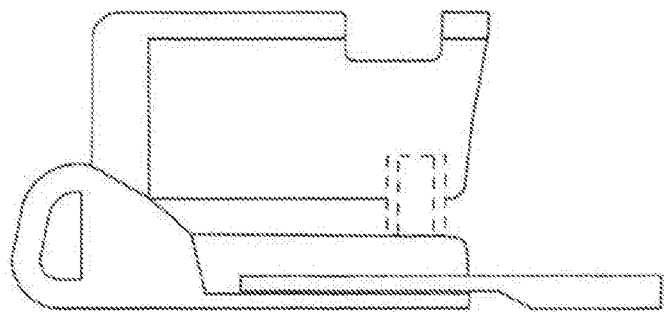
Figure 23:
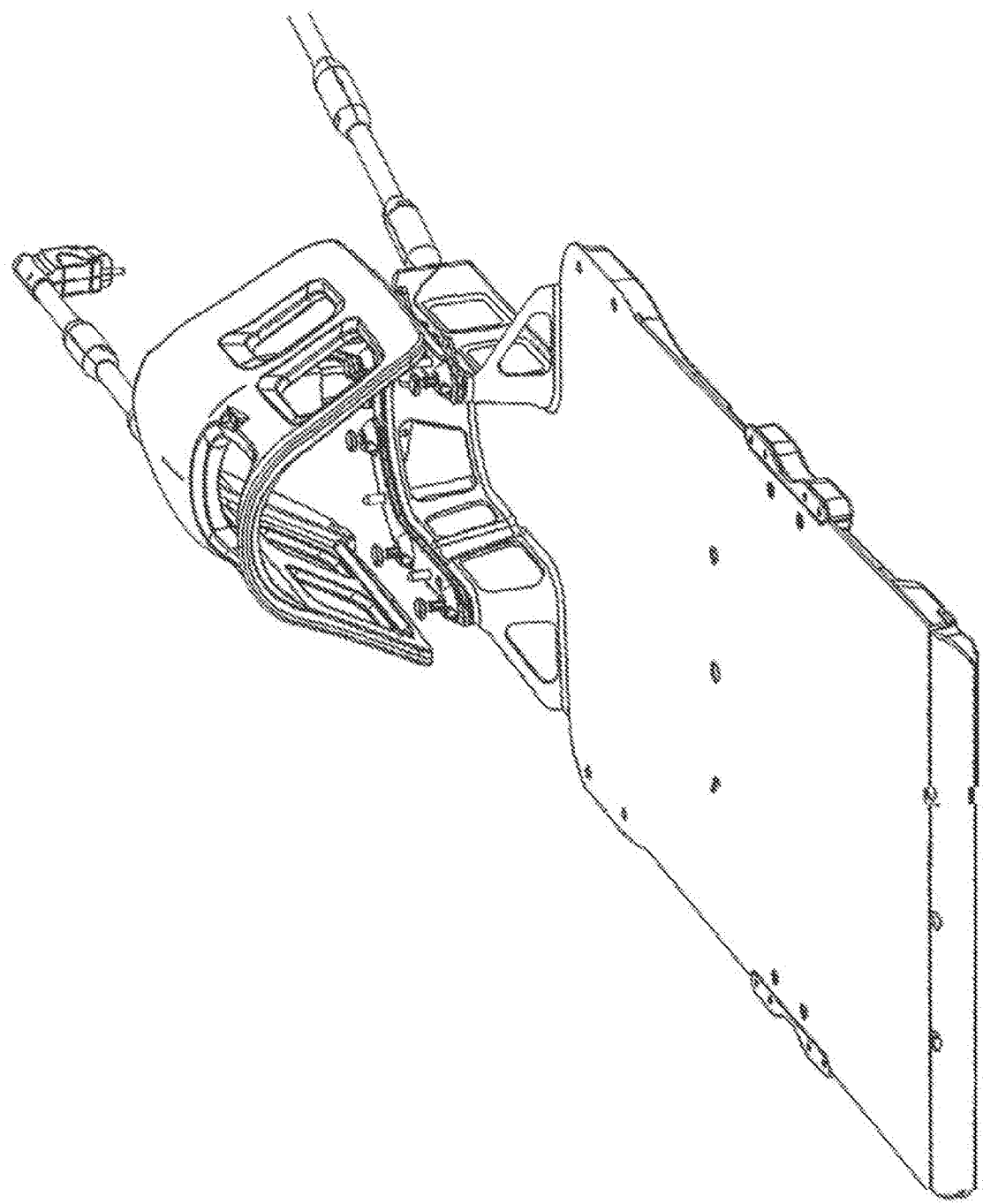
FIG. 23 is a perspective view of the patient positioning apparatus of FIGS. 20-22 with a head portion received by a head coil apparatus.
Figure 24:
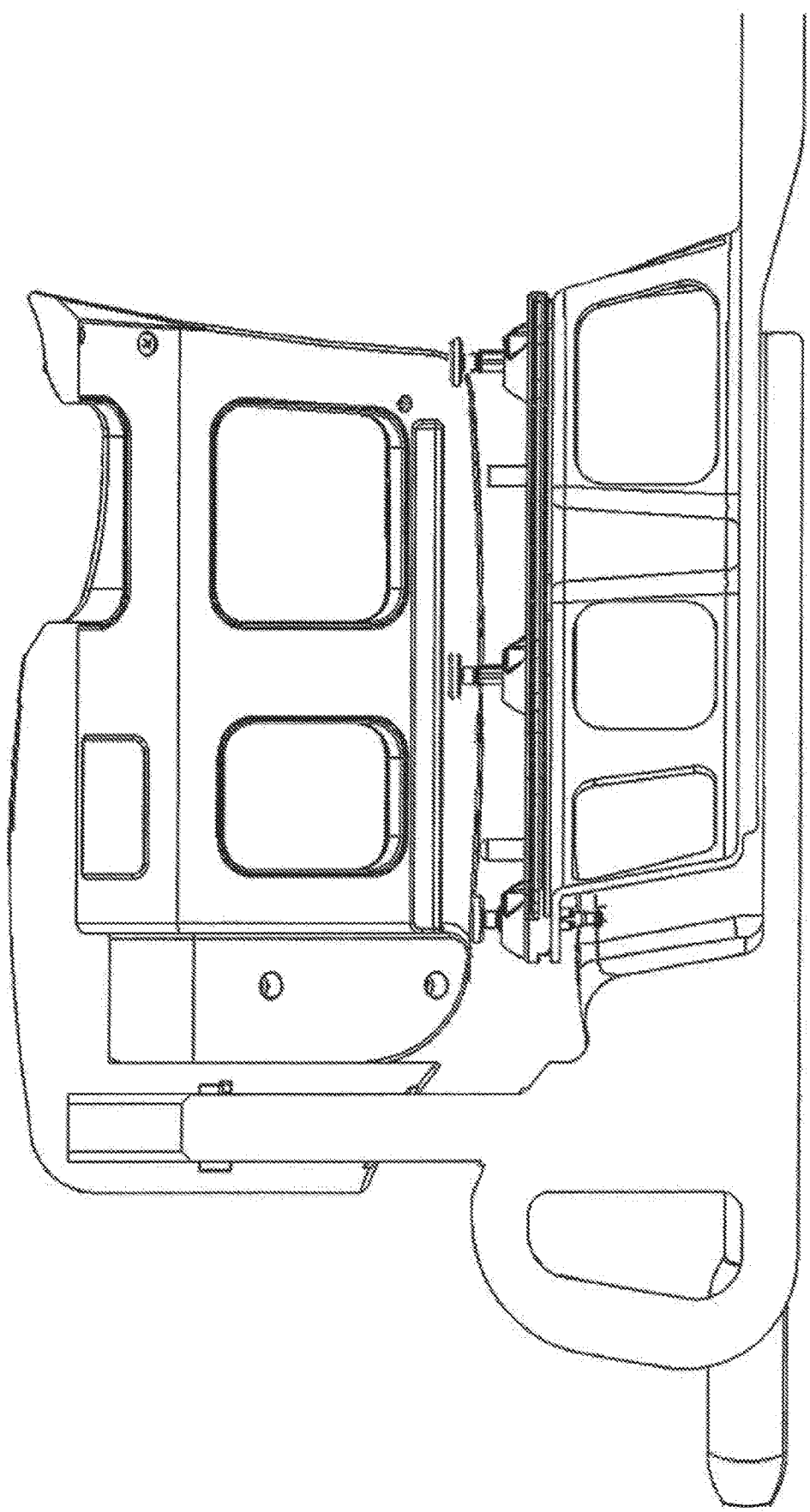
FIG. 24 is a cross-sectional view of a portion of the patient positioning apparatus of FIG. 23 with the head portion received within an internal region of a head coil apparatus.

Arm 160 may include a first arm portion 162*a* having a stud 164 (e.g., a plug) and a second arm portion 162*b* having an inner surface 166 defining a receptacle for receiving stud 164. Preferably, stud 164 and/or inner surface 166 defining the receptacle for stud 164 are configured to rotatably fix base 120 with respect to extension 140. For example, stud 164 may have at least one flat surface and a configuration corresponding to the receptacle defined by inner surface 166, such that first arm portion 162*a* is rotatably fixed with respect to second arm portion 162*b*. In one embodiment, stud 164 has a rectangular configuration that corresponds to a rectangular configuration of the receptacle defined by inner surface 166. Although portable head coil apparatus 100 is illustrated in FIGS. 1 and 14 as containing a single arm 160, in another embodiment, the portable head coil apparatus has a second arm, or a plurality of arms, coupled to the base and the extension. Arms 160 may be positioned on the superior end 102 of apparatus 100, and/or on one or both sides of apparatus 100.

The inventors recognize that in the field of use of portable head coil apparatus 100 (e.g. radiology, radiotherapy simulation) both the importance of quality patient immobilization to ensure minimal imaging artifacts due, for example, to unintended motion as well as the importance of positioning coil arrays 122 and/or 142 as close as possible to the patient to improve signal to noise ratio in order to obtain quality images. The inventors identified that the typical strategy for improving signal to noise ratio focuses on increasing the quantity of coil elements in coil arrays in order to obtain improved signal to noise ratio. However, this strategy is to the exclusion of permitting the use of patient positioning devices due to spatial constraints required in the construction of these coils. Additionally, the conventional focus for some exemplary head coils is to position coil arrays primarily around the crown of the head, which can pose a challenge or render lower image quality when imaging regions in the lower portions of the head and neck.

Portable head coil apparatus 100 advantageously forms an imaging region 126 that positions coil array 122 of base 120 and coil array 142 of extension 140 as close to a patient's head while receiving at least a portion of the patient positioning device within imaging region 126. Additionally, extension 140 and base 120 may retain the coil arrays 122 and/or 142 in an advantageous position relative to one another, regardless of the adjustment of extension 140 relative to base 120 in the anterior/posterior direction, so as to facilitate electronic decoupling and/or to reduce electronic coupling of the adjacent coil elements, improving signal to noise ratio. Portable coil apparatus 100, in a preferred embodiment, accomplishes the forgoing achievements with few components, e.g., with a single coil array 122 contained in housing 123 of base 120 and a single coil array 142 contained in housing 143 of extension 140. This embodiment of portable head coil apparatus 100, against expectations, also provides signal to noise ratio across imaging region 126 encompassing the whole head comparable or superior to that of coil devices in the prior art containing more coil elements than the portable head coil apparatus. This is also achieved over an imaging region 126 that is broader than coil devices in the prior art. FIGS. 47A-47F illustrate, as a comparison, portable head coil apparatus 100 (as configured in this particular embodiment having 15 coil elements) benchmarked against a coil device having a configuration of 8 coil elements and a coil device having a configuration of 20 coil elements.

To this end, base 120 may be configured such that receiving portion 128 and/or receiving surface 130 is positionable proximal a patient's head. As illustrated in FIG. 1, receiving surface 130 of receiving portion 128 is positioned adjacent to a surface of a patient positioning device (e.g., patient positioning device 200) that is opposed a surface that supports the patient head. Receiving surface 130 of base 120 may be spaced from the patient positioning device when the imaging region 126 receives the patient's head supported on the patient positioning device. In an ideal embodiment, however, receiving surface 130 of base 120 contacts a surface of the patient positioning device when the patient positioning device and the patient's head is received in the imaging region 126.

Preferably, portable head coil apparatus 100 is configured to reduce electronic coupling between extension 140 and base 120 when in the imaging position. For example, extension 140 and base 120 may be configured such that at least one of the coil elements 144 of coil array 142 is not parallel to an adjacent one of the coil elements 124 of coil array 122 in the imaging position. Extension 140 and/or base 120 may be configured such that side ends 148*a* and 148*b* extend from center section 156 in planes that are not parallel to planes that side walls 132*a* and 132*b* reside so as to reduce coupling of the coil elements 144 contained in side sections 158*a* and 158*b* and coil elements 124 contained in side walls 132*a* and 132*b*. An overlap of a portion of at least one coil element 124 of coil array 122 of base 120 and a portion of at least one coil element 144 of coil array 142 of extension 140 when the extension 140 is in the imaging position. In addition and/or alternative, the axis of each coil element of portable head coil apparatus 100 is positioned to be substantially normal to the $\beta_0$-magnetic field produced by an imaging system when extension 140 is in the imaging position.

Portable head coil apparatus 100 may form a system with patient positioning device 200. Patient positioning device 200 includes a head portion 240 adapted to support a patient's head. Head portion 240 has a head support surface and an opposed surface. Patient positioning device also includes a body portion 220 coupled to the head portion 240 and adapted to support the body of the patient. Body portion 240 has a body support surface and an opposed surface extending generally in an opposed surface plane. The opposed surface of the head portion is spaced from the opposed surface plane of the body portion, such that the opposed surface of the head portion at least partially defines a space between the opposed surface of the head portion and the opposed surface plane of the body portion.

Portable head coil apparatus 100 of the system includes base 120 having coil array 122 comprising at least two coil elements 124. Base 120 is positionable relative to the patient's head to facilitate imaging of the patient's head by coil array 122, and has a receiving portion 128 defining a receiving surface 130 positionable adjacent patient positioning device 200.

Extension 140 is movable relative to base 120 and has a coil array 142 comprising at least two coil elements 144. Extension 140 defines an inner surface 146 having a concavity the degree of which is greater than that of receiving surface 130 of base 120. Inner surface 146 of extension 140 and receiving surface 130 of base 120 together at least partially define an imaging region 126 therebetween for receiving the patient's head supported on patient positioning device 200. Extension 140 may have a feature adapted to contact a stopping portion of the head portion of the patient positioning device upon lowering extension 140 to a predetermined distance from base 120. Additionally and/or alternatively, the feature may be adapted to contact at least one of the arm of the head coil apparatus, the base of the head coil apparatus, and the patient positioning device when extension 140 is lowered to a predetermined distance from base 120.

In addition, portable head coil apparatus 100 includes arm 160 coupled to base 120 and extension 140. Arm 160 is configured to space base 120 from extension 140 and to adjust the position of extension 140 relative to base 120 between an extended position in which extension 140 is spaced from base 120 and an imaging position 126 in which extension 140 is adjacent to base 120. At least one of the coil elements 144 of coil array 142 of extension 140 is not parallel to an adjacent one of coil elements 124 of coil array 122 of base 120 in the imaging position.

What is claimed is:

1. A portable head coil apparatus for use with a magnetic resonance imaging system, the portable head coil apparatus being configured for unrestricted movement relative to a patient's head supported by a patient positioning device, the portable head coil apparatus comprising:
a base having a coil array including at least two coil elements, the base being positionable relative to the patient's head to facilitate imaging of the patient's head by the coil array, and the base having a receiving portion defining a receiving surface positionable adjacent the patient positioning device;
an extension movable relative to the base and having a coil array including at least two coil elements, the extension defining an inner surface having a curvature the degree of which is greater than that of the receiving surface of the base, wherein the inner surface of the extension and the receiving surface of the base together at least partially define an imaging region therebetween for receiving the patient's head supported on the patient positioning device, the imaging region extending from a superior end of the portable head coil apparatus to an inferior end of the portable head coil apparatus and being accessible from both the superior end and the inferior end of the portable head coil apparatus;
at least one arm coupled to the base and the extension, the at least one arm being configured to space the base from the extension and to adjust the position of the extension relative to the base between an extended position in which the extension is spaced from the base and at least a portion of the extension is not in contact with the base and an imaging position in which the extension is closer to the base and at least a portion of the extension is not in contact with the base; and
wherein the receiving surface of the base is flat, the curvature of the inner surface of the extension forms a parabolic shape, the at least one arm is releasably coupled to at least one of the extension or the base, such that the extension may be mechanically decoupled from the base, and when the extension is mechanically decoupled from the base, the extension is removable, such that the extension has unrestricted movement.

2. The portable head coil apparatus of claim 1, wherein at least one of the coil elements of the coil array of the extension is not parallel to an adjacent one of the coil elements of the coil array of the base in the imaging position.

3. The portable head coil apparatus of claim 1, wherein the receiving surface of the base accepts a patient positioning device, when the imaging region receives the patient's head supported on the patient positioning device.

4. The portable head coil apparatus of claim 1, wherein the extension further comprises an opening adapted to align the coil arrays of the base and the extension with the region of interest and to permit the patient to see out of the coil.

5. The portable head coil apparatus of claim 1, wherein there is an overlap of a portion of at least one of the coil elements of the coil array of the base and a portion of at least one of the coil elements of the coil array of the extension, when the extension is in the imaging position.

6. The portable head coil apparatus of claim 1, the apparatus being configured to align the coil with respect to an isocenter of the magnetic resonance imaging system and to be located by a laser positioning system.

7. The portable head coil apparatus of claim 1, wherein the apparatus can be moved with respect to the patient and an MRI table on which the patient is positioned.

8. The portable head coil apparatus of claim 1, wherein the at least one arm is configured to space the base from the extension via a ratchet mechanism configured to position the extension at a distance from the base.

9. The portable head coil apparatus of claim 1, wherein the at least one arm includes an actuator for releasing and mechanically decoupling the extension from the base in one movement.

10. The portable head coil apparatus of claim 9, wherein the actuator comprises a quick release button.

11. The portable head coil apparatus of claim 1, wherein the at least one arm includes a first arm portion having a stud and second arm portion having an inner surface defining a receptacle for receiving the stud.

12. The portable head coil apparatus of claim 11, wherein one or more of the stud and the inner surface is configured to rotatably hold the extension in a fixed position relative to the base.

13. The portable head coil apparatus of claim 11, wherein the stud includes at least one flat surface and a configuration corresponding to the receptacle defined by the inner surface, such that the first arm portion is rotatably fixed relative to the second arm portion.

14. The portable head coil apparatus of claim 11, wherein the stud has a rectangular configuration corresponding to a rectangular configuration of the receptacle.

15. The portable head coil apparatus of claim 1, wherein the unrestricted movement comprises the extension being moveable toward or away from a patient's head in all degrees of freedom.

16. The portable head coil apparatus of claim 1, wherein the curvature of the inner surface of the extension extends between a first side end and a second side end, wherein when the extension is in the extended position, at least one of the first side end and the second side end is spaced from the base and is not in contact with the base and when the extension is in the imaging position, at least one of the first side end and the second side end is closer to the base and is not in contact with the base.

17. A system including a portable head coil apparatus and patient positioning device comprising:
   a patient positioning device including:
      a head portion adapted to support a head of a patient, the head portion having a head support surface and an opposed surface, and
      a body portion coupled to the head portion and adapted to support the body of the patient, the body portion having a body support surface and an opposed surface extending in an opposed surface plane, wherein the opposed surface of the head portion is spaced from the opposed surface plane of the body portion, such that the opposed surface of the head portion at least partially defines a space between the opposed surface of the head portion and the opposed surface plane of the body portion; and
   a portable head coil apparatus including:
      a base having a coil array including at least two coil elements, the base being positionable relative to a patient's head to facilitate imaging of the patient's head by the coil array, and the base having a receiving portion defining a receiving surface positionable adjacent the head portion of the patient positioning device;
      an extension movable relative to the base and having a coil array including at least two coil elements, the extension defining an inner surface having a curvature the degree of which is greater than that of the receiving surface of the base, wherein the inner surface of the extension and the receiving surface of the base together at least partially define an imaging region therebetween for receiving at least the head portion of the patient positioning device;
      at least one arm coupled to the base and the extension, the at least one arm being configured to space the base from the extension and to adjust the position of the extension relative to the base between an extended position in which the extension is spaced from the base and at least a portion of the extension is not in contact with the base and an imaging position in which the extension is closer to the base and at least a portion of the extension is not in contact with the base; and
      wherein the receiving surface of the base is flat, the curvature of the inner surface of the extension forms a parabolic shape, the at least one arm is releasably coupled to at least one of the extension or the base, such that the extension may be mechanically decoupled from the base, and when the extension is mechanically decoupled from the base, the extension is removable, such that the extension has unrestricted movement.

18. The system of claim 17, wherein at least one of the coil elements of the coil array of the extension is not parallel to an adjacent one of the coil elements of the coil array of the base in the imaging position.

19. The system of claim 17, wherein the base of the head coil apparatus further comprises at least one side wall extending in an upward direction.

20. The system of claim 17, wherein the space between the opposed surface of the head portion and the opposed surface plane of the body portion is positionable adjacent to the receiving portion of the base.

21. The system of claim 17, the head coil being movable relative to the patient.

22. The system of claim 17, wherein the base of the head coil is incorporated into the patient support, such that the receiving surface of the base corresponds to an upper plane of an MRI table.

23. The system of claim 17, wherein the receiving surface of the base is coplanar to the upper surface of the patient support.

24. The system of claim 17, wherein in an imaging position, one of the base or the extension of the head coil apparatus is positioned posterior to the head of the patient and the other of the base or the extension is positioned anterior to the head of the patient.

25. The system of claim 17, wherein in the imaging position, the portion of the base of the head coil apparatus extends into the space at least partially defined by the head portion of the patient positioning apparatus.

26. A method of positioning a system including a portable head coil relative to a patient for imaging, the method comprising:
   positioning a patient positioning device on a surface of a patient support such that an opposed surface of a head portion of the patient positioning device at least partially defines a space between the opposed surface of the head portion of the patient positioning device and the surface of the patient support;
   positioning a patient on the patient positioning device;
   providing the portable head coil apparatus of claim 1;
   positioning the base including the coil array of the base to facilitate imaging of the patient by the coil array of the base by moving the base in a positioning direction;
   positioning the extension including the coil array of the extension to facilitate imaging of the patient by the coil array of the extension by moving the extension relative to the base along an extending direction, thereby at least partially defining an interior region for receiving a body part of the patient to be imaged, the extending direction being orthogonal to the positioning direction; and
   retaining a selected distance between the coil array of the base and the coil array of the extension along the extending direction, thereby maintaining the size of the interior region at least partially defined by the extension and the base.

27. The method of claim 26, further comprising moving the base to the patient positioned on the patient positioning device such that an interior receiving portion of the head coil receives the head of the patient and the head portion of the patient positioning device with at least a portion of a base of the head coil and at least a portion of at least one coil array of the head coil received in the space defined between the opposed surface of the head portion of the patient positioning device and the surface of the patient support.

28. The method of claim 26, further comprising positioning the base and the extension such that the head of the patient extends into the interior region defined by the base and the extension.

29. The method of claim 26, further comprising positioning the base and the extension relative to a patient positioning apparatus.

30. The method of claim 29, further comprising aligning the patient positioning apparatus, the base, and the extension relative to an imaging scanner using a laser positioning system.

* * * * *